(12) United States Patent
Hung et al.

(10) Patent No.: US 6,689,070 B2
(45) Date of Patent: *Feb. 10, 2004

(54) DEVICES, METHODS AND SYSTEMS FOR COLLECTING MATERIAL FROM A BREAST DUCT

(75) Inventors: David Hung, Belmont, CA (US); Philip M. Olsen, Cupertino, CA (US); Daniel R. Kurz, Sunnyvale, CA (US)

(73) Assignee: Cytyc Health Corporation, Boxborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/109,046

(22) Filed: Mar. 29, 2002

(65) Prior Publication Data

US 2002/0169391 A1 Nov. 14, 2002

Related U.S. Application Data

(63) Continuation-in-part of application No. 09/473,510, filed on Dec. 28, 1999, now Pat. No. 6,413,228.
(60) Provisional application No. 60/283,636, filed on Apr. 16, 2001, provisional application No. 60/114,048, filed on Dec. 28, 1998, provisional application No. 60/134,613, filed on May 18, 1999, provisional application No. 60/143,476, filed on Jul. 12, 1999, provisional application No. 60/143,359, filed on Jul. 12, 1999, and provisional application No. 60/170,997, filed on Dec. 14, 1999.

(51) Int. Cl.[7] .............................. A61B 10/00; A61B 5/00
(52) U.S. Cl. ..................... 600/562; 600/573; 604/28; 435/7.23
(58) Field of Search ................................ 600/562, 573, 600/576, 581; 435/7.21, 7.23; 604/28, 30, 35, 104, 264; 119/14.19

(56) References Cited

U.S. PATENT DOCUMENTS 4,023,559 A    5/1977  Gaskell
5,012,818 A  * 5/1991  Joishy ........................ 600/567
6,413,228 B1 * 7/2002  Hung et al. ................. 600/562

FOREIGN PATENT DOCUMENTS

| EP | 0 250 891 | 1/1988 |
| EP | 0 547 463 | 6/1993 |
| WO | WO 99/65546 | 12/1999 |
| WO | WO 00/20031 | 4/2000 |
| WO | WO 00/39557 | 7/2000 |

OTHER PUBLICATIONS

Hou et al., A Simple Method of Duct Cannulation and Localization for Galactography before Excision in Patients with Nipple Discharge, Radiology, 1995, pp 568–569, vol. 195.
Papanicolaou, et al., Exfoliative Cytology Of The Human Mammary Gland And Its Value In The Diagnosis Of Cancer And Other Diseases Of The Breast, Cancer, Mar.–Apr. 1958, pp. 377–409, vol. 11.
Jama, Breast fluid cells help in early cancer detection, May 7, 1973, pp 823–827, vol. 224, No. 6.
Love, et al, Breast–duct endoscopy to study stages of cancerous breast disease, The Lancet, Oct. 12, 1996, pp 997–999, vol. 348.

* cited by examiner

Primary Examiner—Charles Marmor
(74) Attorney, Agent, or Firm—Banner & Witcoff

(57) ABSTRACT

The invention provides methods, devices and systems for collecting breast ductal fluid comprising cellular material and other useful markers for analysis. The methods typically comprise access of at least one breast duct and collecting materials from that duct separate from all other ducts in the breast. The devices comprise ductal access devices that provide the opportunity to collect fluid from a single duct separate from all the other ducts in the breast. The systems employ the methods and devices that used together provide systems for analysis of a breast condition in a patient specific to accessed breast ducts. The methods, devices and systems are particularly useful for identification of breast precancer or cancer in within the patient.

77 Claims, 12 Drawing Sheets

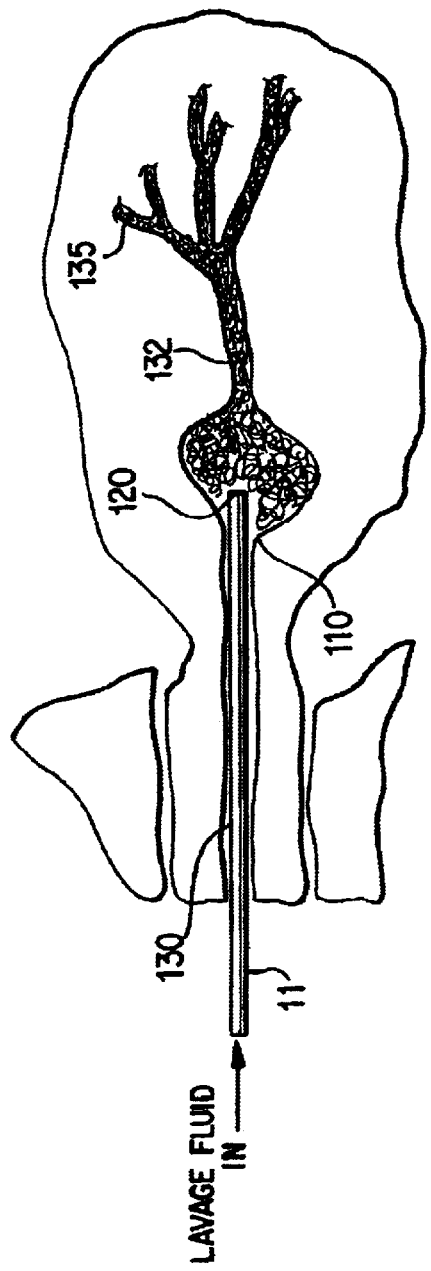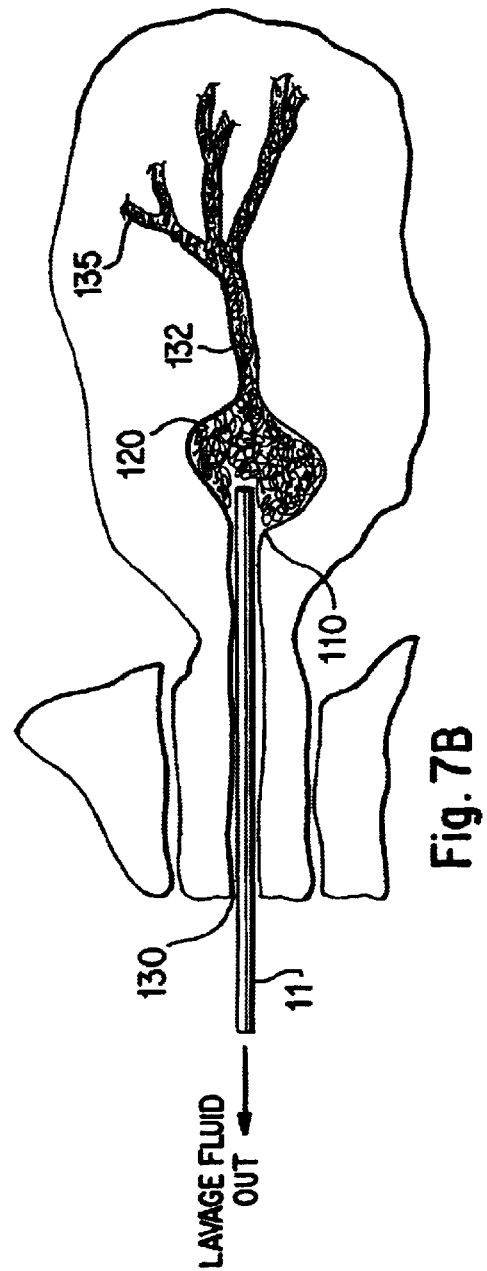

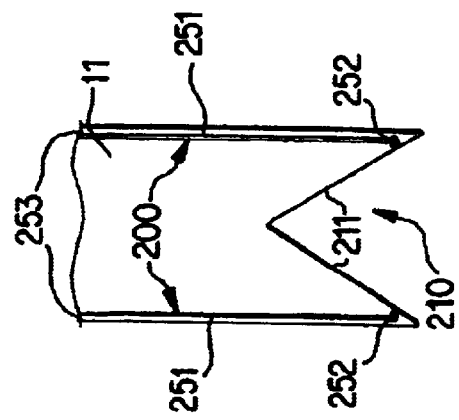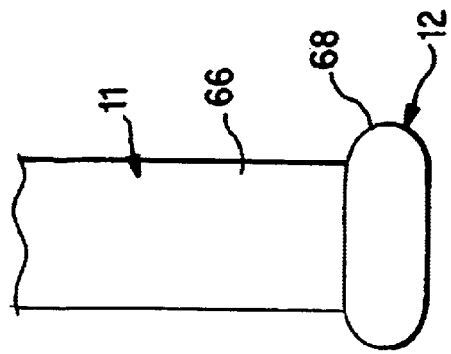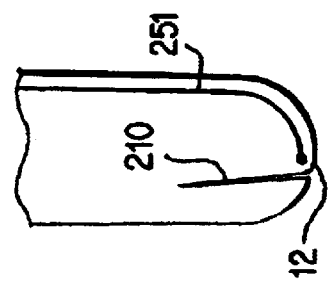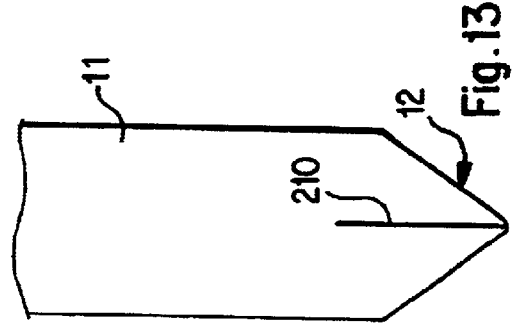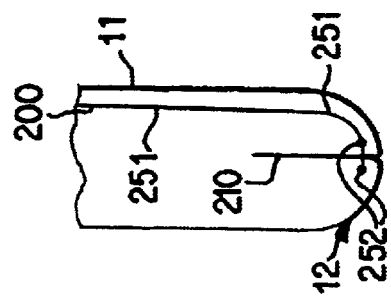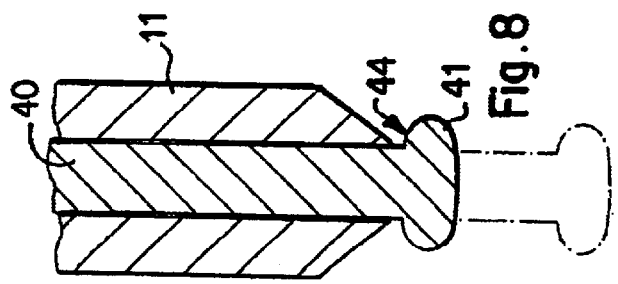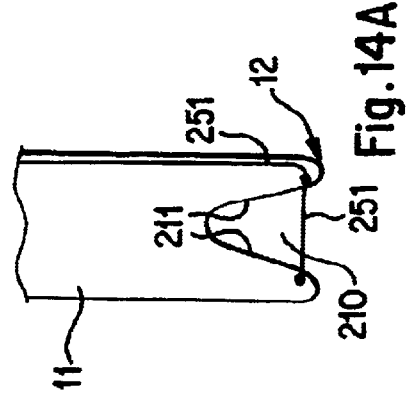

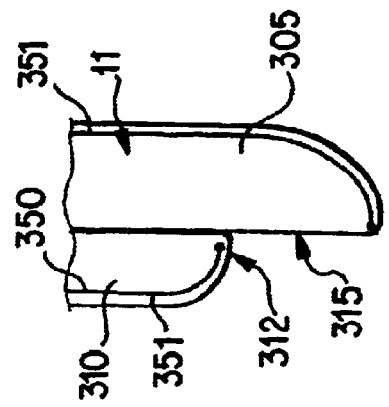
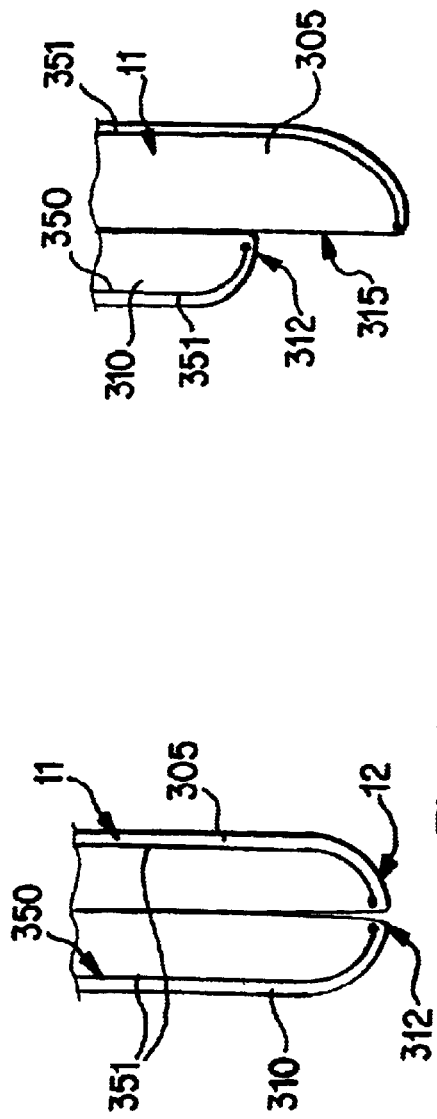
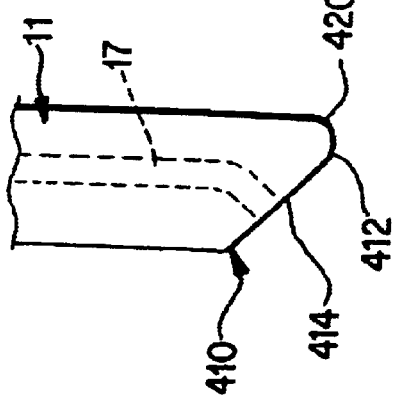
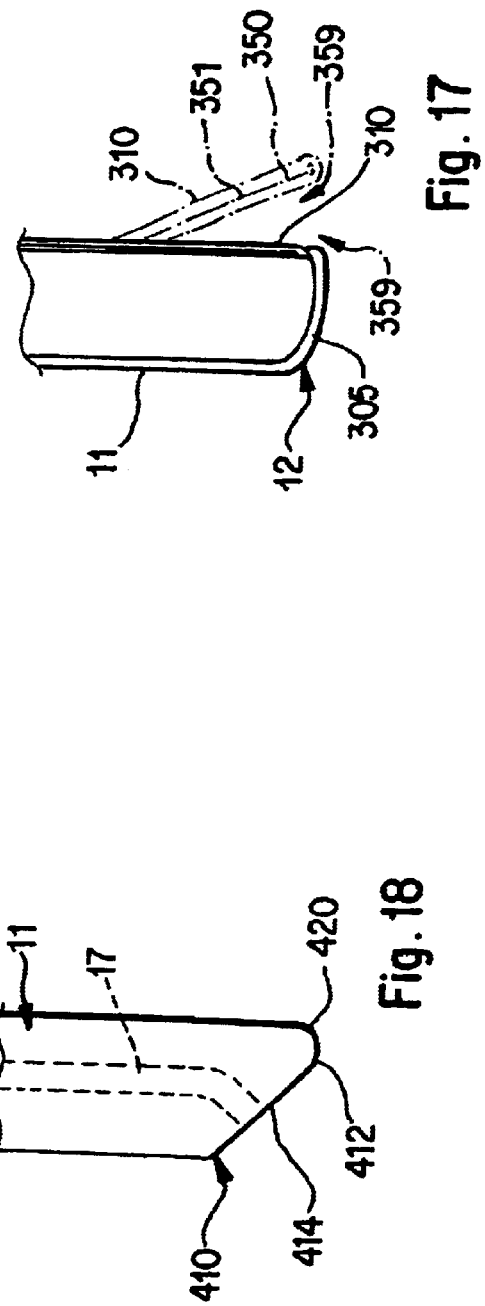

DEVICES, METHODS AND SYSTEMS FOR COLLECTING MATERIAL FROM A BREAST DUCT

CROSS-REFERENCES TO RELATED APPLICATIONS

Benefit of the Apr. 16, 2001 filing date of Provisional Application Serial No. 60/283,636, is hereby claimed. This application is a continuation-in-part of U.S. patent application Ser. No. 09/473,510, filed on Dec. 28, 1999, now U.S. Pat. No. 6,413,228, and each of the following provisional applications under 37 CFR §1.78: Nos. 60/114,048, filed on Dec. 28, 1998; 60/134,613, filed on May 18, 1999; 60/143,476, filed on Jul. 12, 1999; 60/143,359, filed on Jul. 12, 1999; and 60/170,997, filed on Dec. 14, 1999. The full disclosures of each of these applications are incorporated herein by reference.

The present invention relates to medical devices, methods and systems for introducing fluids into and collecting a composition from a duct within a mammalian breast. More particularly, the present invention relates to medical devices, methods and systems for accessing the duct within the breast, introducing fluid within the duct, retrieving a composition from within the duct and passing the composition out of the breast so that it can be collected and analyzed without injuring the ducts within the breast or any other part of the breast.

BACKGROUND OF THE INVENTION

Breast cancer is the most common cancer in women, with well over 100,000 new cases being diagnosed each year in the United States alone. Breast cancer usually begins in the cells lining a breast duct (epithelial lining), with the first stage of the cancer thought to include the excessive proliferation of individual cell(s) that lead to "ductal hyperplasia." Some of the hyperplastic cells may then become atypical, with a significant risk of the atypical hyperplastic cells becoming neoplastic or cancerous. Initially, the cancerous cells remain in the breast ducts, and the condition is commonly referred to as ductal carcinoma in situ (DCIS). After a time, however, the cancerous cells begin to invade outside of the ductal environment, presenting the risk of metastases, which, as is well known, can be fatal to the patient.

While breast cancer through the DCIS phase is in theory quite treatable, early diagnosis is critical to the effectiveness of the chosen treatment. At present, mammography is the most well known diagnostic tool for detecting breast cancer. However, mammography is often only able to detect tumors that have reached a size in the range from 0.1 cm to 1 cm. Such a tumor mass may not be reached until 8 to 10 years following initiation of the disease process. Detection of breast cancer at such a late stage is often too late to permit effective treatment. As a result, alternative diagnostic modalities that promise much earlier detection of breast cancer are needed.

Breast cancer is believed to originate in the lining of fluid producing breast milk ducts in the breast; and additionally human breasts are believed to contain from 6 to 8 of these ducts. See Sartorius, *JAMA* 224 (6): 823–827 (1973). Therefore, in a search for an answer for early detection, significant members of the medical community dedicated to studying breast cancer have believed and shown that the cytological analysis of cells retrieved from nipple discharge from the breast milk ducts can provide valuable information leading to an early identification of patients who are at risk for breast cancer. Indeed Papanicolaou contributed to the genesis of such a possibility of a "Pap" smear for breast cancer by analyzing the cells contained in nipple discharge that collected on the outer surface of the nipple. See Papanicolaou et al, "Exfoliative Cytology of the Human Mammary Gland and Its Value in the Diagnosis of Cancer and Other Diseases of the Breast" Cancer (1958) March/April 377–409.

Other attempts to find an early detector include Sartorious's use of hair-like, single lumen fluid introduction catheters that were inserted into breast ducts using an operating microscope so that the ducts could be flushed with saline solution. After the fluid was introduced, the single lumen catheter was removed and the breast was squeezed so that fluid would be expelled out of the breast through the nipple. The expelled fluid typically collected on the outer surface of the nipple and was removed by a capillary tube positioned against the nipple. Similarly, Love and Barsky, "Breast-duct endoscopy to study stages of cancerous breast disease", *Lancet* 348 (9033):997–999, 1996 describes cannulating breast ducts with a single lumen catheter and infusing a small amount of saline, removing the catheter and squeezing to collect the fluid that returns onto the outer surface of the nipple. Additionally, in "A simple method of Duct Cannulation and Localization for Galactography before Excision in Patients with Nipple Discharge." *Radiology* 1995; 195; 568–569 Hou et al. describes injecting a "small volume of sterile, water soluble contrast material . . . (0.5 ml–2.0 ml) . . . the catheter was taped on the breast or nipple . . . the contrast material was aspirated with the same syringe and gentle manual pressure was exerted on the breast to expel the opaque medium."

Diagnostics, Inc developed another example of a similar process for obtaining ductal fluid for cytology. This company produced devices that could be used to obtain breast ductal fluid for cytological evaluation. The devices included a hair-like single lumen breast duct catheter to infuse fluid into a breast duct and the procedure dictated that after removal of the catheter oozing fluid was collected from the nipple surface with a capillary tube. The devices were sold prior to May 28, 1976 for the purpose of collecting breast ductal fluid for cytological evaluation.

While the above-mentioned disclosures contemplate introducing fluid into a breast duct, they rely on externally applied pressure to expel fluid from within the duct. However, when the expelled fluids accumulate on the exterior of the nipple, it is very difficult, if not impossible, to determine the individual duct that expelled the fluid having the atypical or cancerous cells. Therefore, if the cytological examination comes back positive, it is very unlikely that the duct that produced the fluid can be identified and treated. Alternatively, in other instances, the ductal sphincter may prevent a necessary amount of ductal fluid that is needed for a useful sample from being expelled and collected. Additionally, the sphincter may block some of the cells from being passing out through the nipple.

SUMMARY OF THE INVENTION

The present invention includes devices and methods for obtaining ductal fluids and cellular material from a ductal network in a human breast in order to determine if the patient has or is likely to develop breast cancer. The devices and methods of the present invention permit the fluids and cellular material to be collected without collapsing the duct.

In a first embodiment of the present invention, the device for accessing a mammalian duct and collecting cellular material from within the duct comprises a catheter that can be positioned within the duct and a manifold lumen. The catheter includes a proximal end and a distal end. The distal end has an opening for delivering lavage fluid within the duct and receiving cellular material from within the duct. The manifold hub is in fluid communication with the catheter. The manifold hub comprises a distal end having a first port that is axially aligned with an internal lumen of the catheter, a second port positioned within the hub for infusing fluids into hub and a third port positioned within the hub for collecting fluid from within the hub.

In another aspect of the invention, the ductal access device comprises an elongated member that can be positioned within the breast duct. The elongated member comprises an internal lumen that is in fluid communication with a manifold hub.

The present invention also includes a ductal access device for accessing a breast duct and collecting cellular material from within the duct. The device comprises an elongated member including a proximal end, a distal end and a lumen extending between the proximal and distal ends. The device also includes a hub comprising an infusion port for delivering fluid to the lumen of the elongated member. The infusion port is in fluid communication with an infusion device. The device further includes a collection port for receiving fluid and cellular material from within the hub.

Another aspect includes a ductal access device for accessing a breast duct and collecting cellular material from within the duct. The device comprises a first elongated member having a first outer diameter for positioning within the breast duct and a second elongated member having a second outer diameter that is greater than the first outer diameter. The second outer diameter creates a stop along the length of the device that prevents the second elongated member from entering the breast duct.

The present invention also includes a ductal access device for accessing a breast duct and collecting cellular material from within the duct. The device comprises a first elongated member having a proximal end, a distal end and an internal lumen extending between these ends. The device also comprises a manifold hub having a proximal end and a distal end. The manifold hub also has a lower opening that is in fluid communication with the internal lumen. An elongated guide member extends through at least one of the first elongated member and the hub for positioning a portion of the first elongated member in the breast duct.

A further aspect of the present invention includes a ductal access device for accessing a breast duct and collecting cellular material from within the duct. The device comprises a first elongated member having a distal end that can move between an open position and a closed position, a proximal end and an internal lumen extending between these ends. The device also comprises a manifold hub having a proximal end and a distal end. The manifold hub also has a lower opening for being in fluid communication with the internal lumen.

A method for lavaging a ductal network in a human breast according to the present invention comprises the steps of inserting a distal end of a catheter having an internal lumen through a ductal orifice and into a distal lumen of the ductal network, infusing a lavage fluid into a manifold hub through an infusion port and introducing the lavage fluid into the ductal network. The method also includes the steps of withdrawing the lavage fluid and substances borne by the lavage fluid from the ductal network and delivering the withdrawn fluid and substances to a collection device through a collection port in the hub.

Another method for obtaining cellular material from a mammalian breast duct network according to the present invention includes the steps of inserting a distal end of an elongated device having an internal lumen through a ductal orifice and into a distal lumen of the ductal network, infusing a lavage fluid into a manifold hub through an infusion port and introducing the lavage fluid into the ductal network through the lumen. The method also includes the steps of massaging an area of the breast and delivering the lavage fluid and substances borne by the lavage fluid from the ductal network to a collection device through a collection port in the hub.

One aspect of the present invention relates to medical devices and methods for obtaining a cellular material carried by a fluid from within a breast duct so that the recovered cellular material can be analyzed for the presence of a-typical, pre-cancerous or cancerous cells. Another aspect of the present invention relates to a medical device that allows for a lavage fluid, such as saline, to be introduced into a breast duct and retrieved from the breast duct without the device being removed from the duct and without injuring the breast or the duct in which the device is positioned. A further aspect of the present invention relates to a method for safely and effectively lavaging the duct by introducing the lavage fluid into the duct, mixing the lavage fluid with cellular material within the duct and retrieving a composition of previously existing ductal fluid, at least a portion of the infused lavage fluid and the cells separated from the epithelial lining of the duct.

BRIEF DESCRIPTION OF THE DRAWINGS

FIG. 7A illustrates filling a duct with infusion fluid;

FIG. 7B illustrates bidirectional flow of infused fluid in the duct through the access lumen to be collected;

FIG. 8 illustrates a dilator according to the present invention having an atraumatic tip;

FIG. 9 illustrates a catheter according to the present invention having an atraumatic tip;

FIG. 13 illustrates a catheter formed of a shape memory material and having a distal end that can move between an open position and a closed position;

FIG. 14 illustrates a catheter having an open end and an opening system;

FIGS. 14A–14C illustrate alternative embodiments of the catheter illustrated in FIG. 14;

FIG. 15 illustrates an openable catheter having a sliding portion in a closed position;

FIG. 16 illustrates an openable catheter having a sliding portion in an open position;

FIG. 17 illustrates another embodiment of an openable catheter having a sliding portion in an open position;

FIG. 18 shows an alternative embodiment of a catheter; and

DETAILED DESCRIPTION OF THE FIGURES

The following embodiments and examples are offered by way of illustration and not by way of limitation.

Figure 1:
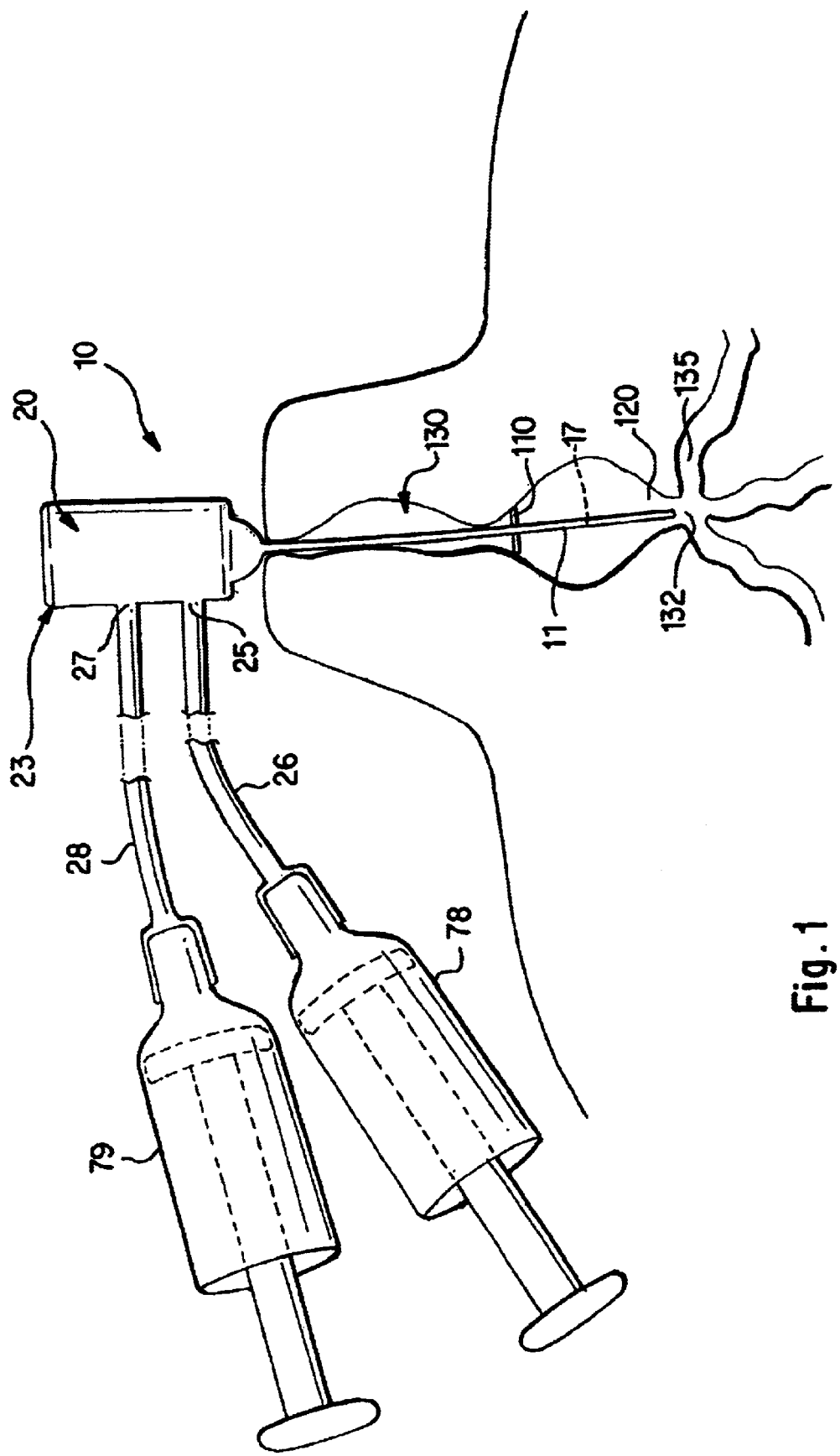
FIG. 1 shows a ductal access device according to the present invention inserted in a breast duct.

As is well known and as shown in FIG. 1, a female breast includes a plurality of milk ducts. Currently, it is believed that a breast includes between 6 and 8, possibly more, milk ducts. The nipple of each breast includes an array of ductal orifices. Each ductal orifice corresponds to one of the milk ducts and provides an opening to its respective duct. Each duct includes a lactiferous sinus located between the braches of the duct and its respective ductal orifice. Additionally, a sphincter is located at the end of the lactiferous sinus that is proximate the nipple for preventing fluid within the breast duct from unintentionally leaking out through the nipple. The sphincter also maintains a level of pressure within the duct that keeps the duct from collapsing. Fluid collected from one or more of these breast ducts can provide valuable information that may lead to identifying whether or not that patient has or is at risk for breast cancer.

Figure 2:
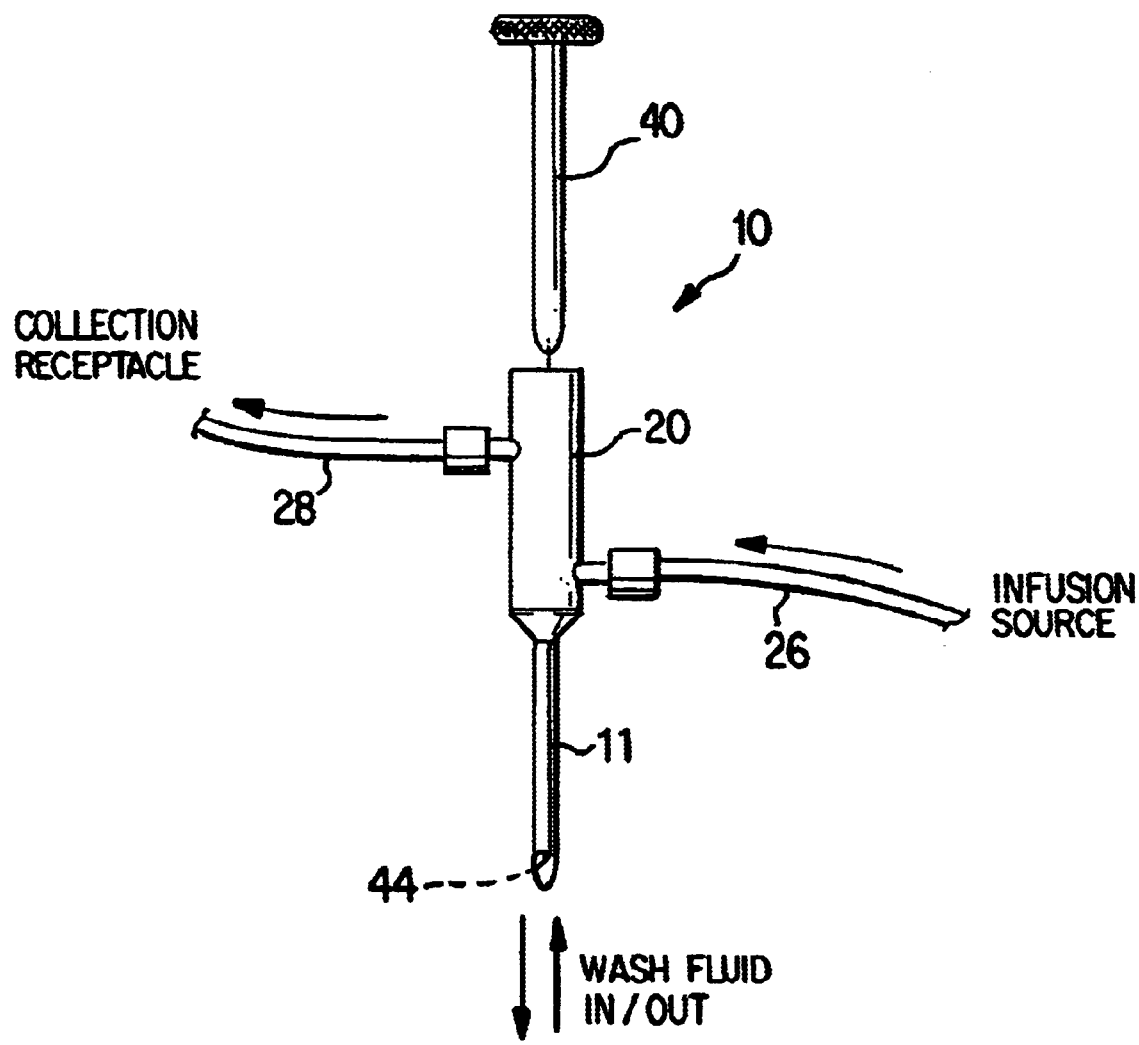
FIG. 2 illustrates a ductal access device having a hub, catheter, infusion and collection lumens and a retractable dilator.

FIG. 2 illustrates a ductal access device 10 for introducing the lavage (wash) fluid into the breast duct and retrieving a composition that includes a mixture of all, some or at least one of the following: the introduced lavage fluid, fluid present within the duct before the introduction of the lavage fluid, naturally occurring fluid that develops within the duct in the presence of the access device 10 and/or the lavage fluid, and cellular material from the duct including cellular material from the epithelial lining. The term "lavage fluid" refers to a fluid that can be introduced into a breast duct to wash cells from the epithelial lining of the duct and/or mix with these cells and other cells that may already have fallen from the ductal lining in order to wash the cells from the duct. Saline is an example of a known fluid that can be used as a lavage fluid. Other examples of known fluids that can be used as lavage fluids are discussed below.

Figure 3:
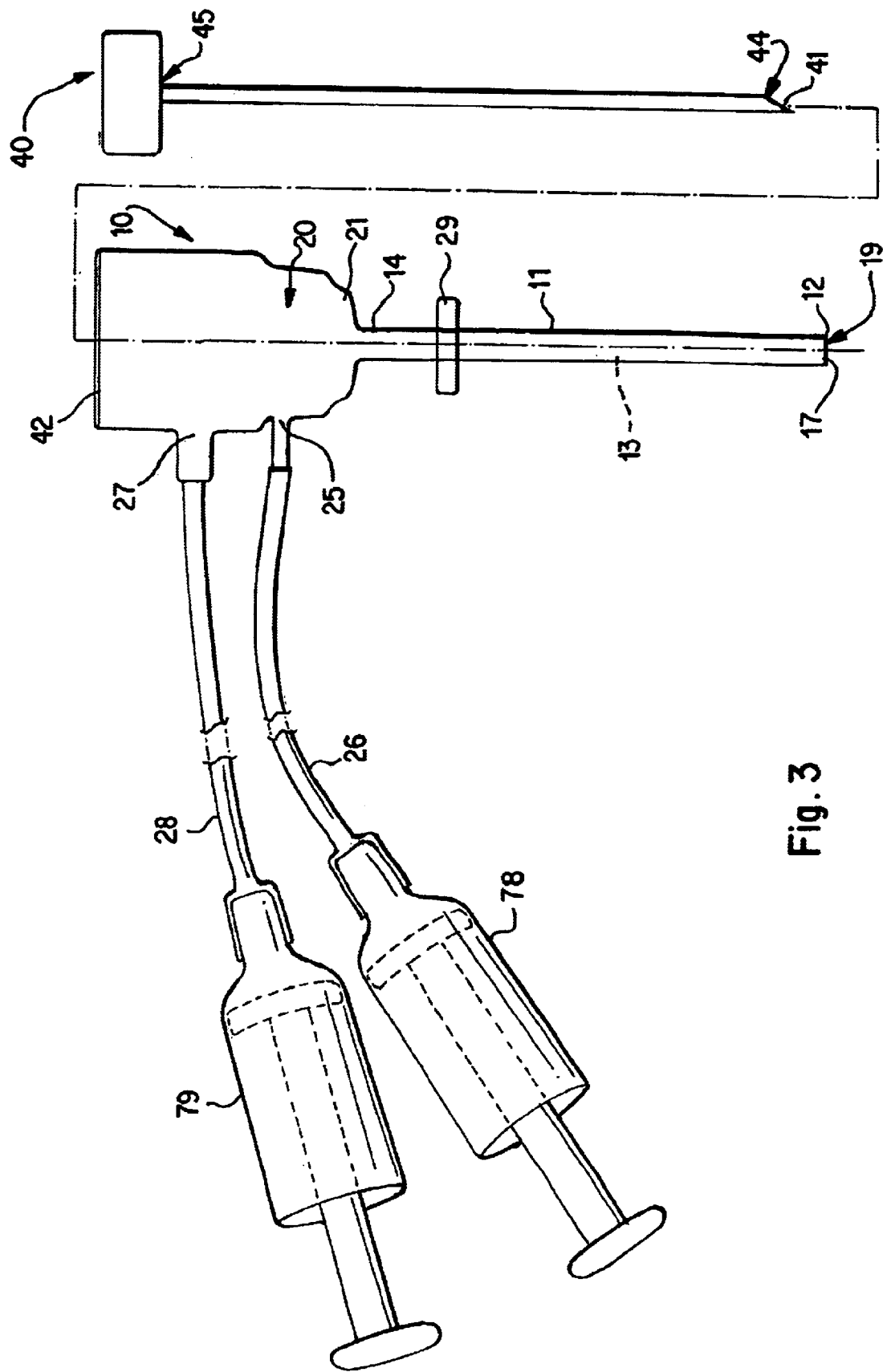
FIG. 3 is a schematic view of a ductal access device according to the present invention.

As shown in FIG. 1, the ductal access device 10 introduces the lavage fluid within the breast duct 130 and retrieves the composition without collapsing or otherwise injuring the duct 130. This is accomplished by creating a pressure differential between the ductal access device 10 and the duct 130. As discussed below, this pressure differential includes a first, elevated fluid pressure level within the duct 130 and a second, lower fluid pressure level within the access device 10. The established pressure differential maintains the pressure within the duct 130 at a level that is substantially equal to or greater than the pressure that naturally exists within the duct 130 prior to the infusion of the lavage fluid, as the ductal fluid is being removed from within the duct for collection. The lower pressure within the access device 10, as compared to the pressure within duct 130, for example as a result of external force being applied to the breast, encourages the composition to exit the duct 130 without causing an internal ductal pressure that is below normal ductal pressure. As a result, the duct 130 will not collapse. The area of lower pressure may be established at a location outside the duct 130, such as shown in FIG. 3, or within an isolated chamber positioned within the duct 130. Additionally, the area of low pressure causes the retrieved composition to naturally flow along the path of least resistance to the second, low-pressure area where it can be collected for analysis. The pressure differentials can be between about 0.1 psi and 5.0 psi.

As shown in FIG. 3, the ductal access device 10 comprises a single lumen elongated ductal access member 11, for example a catheter or stent, (herein after referred to as "catheter") and a hub 20. The catheter 11 has a first, distal end 12 that is introduced into the breast duct 130 for establishing a pathway for the lavage fluid to enter the duct 130 and the composition to be retrieved from the duct 130. A port 19 is located proximate the first end 12 of the catheter 11 so that it opens in the direction of the breast duct. In a preferred embodiment, the port 19 has an opening that extends diametrically across the catheter 11. However, other openings such as those that extend in a direction that is parallel to the length of the catheter 11 could also be used. The catheter 11 also has a second, proximal end 14 that is opposite the distal end 12. An internal lumen 13 extends through the interior of catheter 11 between ends 12, 14. The internal lumen 13 has an inner diameter of between about six thousandths of an inch and thirty thousandths of an inch. In a preferred embodiment, the inner diameter is about twenty-five thousandths of an inch. In another preferred embodiment, the inner diameter is about twenty thousandths of an inch. The catheter 11 also has wall thickness of about five thousandths of an inch. However, by making the wall thickness as small as possible, the inner diameter can be increased for the same overall outer diameter. The catheter 11 has an overall length of between about ten and twenty-five millimeters. In a preferred embodiment, the working length of the catheter 11 is about fifteen millimeters. In other preferred embodiments, it is longer, for example up to about twenty-five millimeters. These distances permit a predetermined lavage position to be achieved.

The second, proximal end 14 of the catheter 11 opens into the hub or well 20 (herein after "hub") as shown in FIG. 3. At the proximal end 14, an opening of the internal lumen has a diameter of between about six and about thirty thousandths of an inch. In a preferred embodiment, the inner diameter is about twenty-three thousandths of an inch. The catheter 11 has an outer diameter of between about ten and forty thousandths of an inch. In a preferred embodiment, the outer diameter is about thirty-five thousandths of an inch.

As seen in FIG. 3, the proximal end 14 of the catheter 11 terminates at a distal end 21 of the hub 20. Alternatively, the proximal end 14 could be positioned so that it extends into the hub 20 or the proximal end 14 could terminate before reaching the distal end 21 of hub 20. If the catheter 11 terminates before the distal end 21, the catheter 11 can be connected to the hub 20 by a connecting conduit section or other type of fluid passageway. No matter the connection between the proximal end 14 of the catheter 11 and the distal end 21 of the hub 20, the distal end 21 of the hub 20 has an outer diameter of about four millimeters and an inner diameter of about three millimeters. The wall thickness is about one-half millimeter. The outer diameter at the distal end of the connecting conduit section is about three millimeters.

Figure 4:
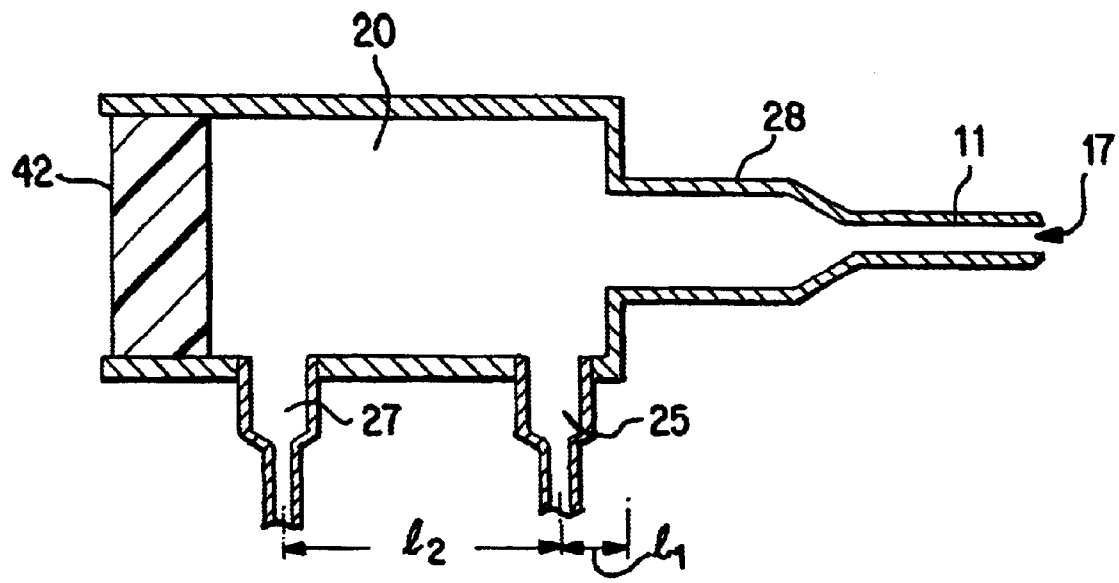
FIGS. 4–6 are cross sectional views of ductal access devices according to the present invention.
Figure 5A:
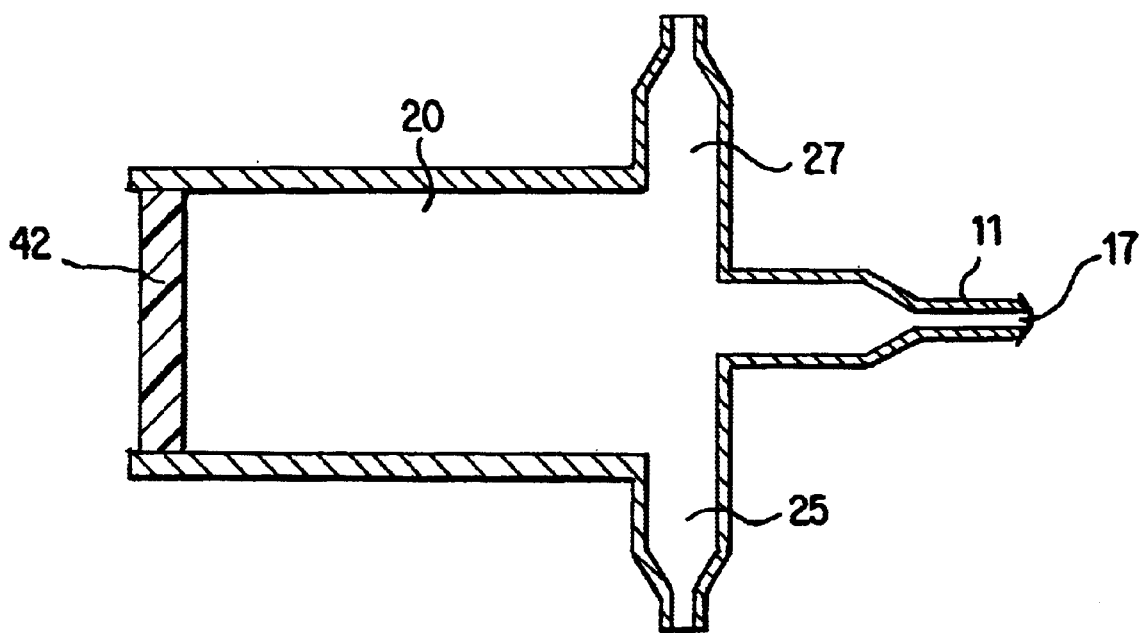
Figure 5B:
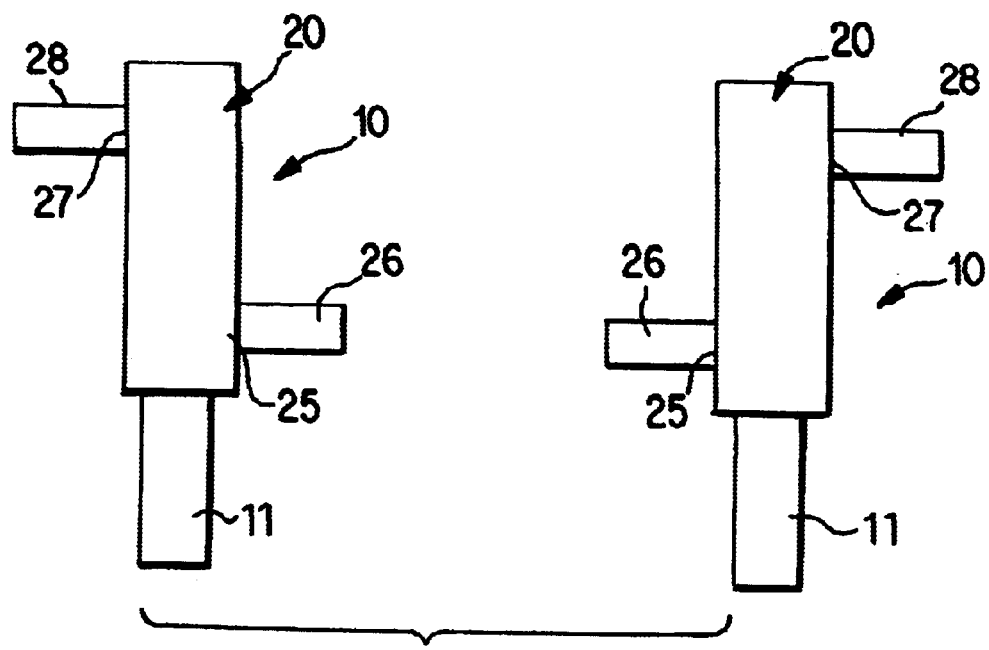

The hub 20 also includes an infusion port 25 and a collection port 27 as shown in FIGS. 3–5. Each of these ports 25, 27 is connected to any known fluid line such as a tube. While the following embodiments will be disclosed with respect to tubes 26, 28 being connected to these ports 25, 27, any type of fluid conduit could be secured to the ports 25, 27, or integrally formed with the ports 25, 27 as a continuous one-piece member, as would be understood by one of ordinary skill in the art. The infusion port 25 is connected and secured to an infusion tube 26 from which fluid is infused into the hub 20 and the catheter 11. A collection tube 28 from which fluid is collected from the catheter 11 and the hub 20 is secured to the collection port 27.

The infusion tube 26 can have any length, for example it can be between about 0.25 inch and 4 feet long, and it can be connected to an infusion syringe 78 or other infusion mechanism for infusing lavage fluid into the breast duct. Similarly, the collection tube 28 can have any length, for example it can be between about 0.25 inch and 4 feet long, and it can be connected to a collection conduit, a collection syringe 79, or other collection device for collecting the composition as it is drawn into the hub 20. The infusion syringe 78 and the collection syringe 79 can be secured or otherwise attached to their respective tubes 26, 28 in any known manner including luer locks, friction fitting or an interference fit.

The infusion port 25 is positioned as close to the proximal end 14 of the catheter 11 as possible. In a preferred embodiment, the infusion port 25 is located adjacent the distal end 21 of the hub 20 so that the distance separating them is minimized. If the infusion port 25 is spaced from the opening of the distal end 21, it is only separated there from by a distance $l_1$ that is needed for the structural integrity of the distal end 21, such as 0.0375 inch or less. In an alternative embodiment, the infusion port 25 can be spaced from the distal end 21 by a distance of about one millimeter or less. In a preferred alternate embodiment, this distance is about one-half or one-quarter millimeter.

As illustrated in FIG. 4, the infusion and connection ports 25, 27 are spaced from each other so that the lavage fluid may be infused through the infusion port 25 and simultaneously removed through the collection port 27. The collection port 27 is positioned at the same distance or further away from the distal end 21 than the infusion port 25. Hence, the collection tube 28 is attached to the hub 20 at a position no closer to the catheter 11 than the infusion tube 25. The ports 25, 27 are spaced from each other by a distance $l_2$ that can be from about 0 to 0.010 inch, preferably being about 0.0375 inch or less. In the embodiment of FIG. 4, the distance between the collection port 27 and the proximal end of the hub 20 is about two millimeters.

The infusion port 25 can have any longitudinal position and circumferential position within the hub 20 relative to the collection port 27. For example, as shown in FIG. 5, the infusion port 25 and the collection port 27 can be at the same height along the inner wall of the hub 20, but offset from each other by a number of degrees, such as 90 or 180 degrees. When the ports 25, 27 are offset by 180 degrees, they are positioned across the hub 20 from each other as shown in FIG. 5. In another embodiment, the collection port 27 could be located above the infusion port 25 along the sidewalls of the hub 20. The collection port 27 could be longitudinally aligned with the infusion port 25 or circumferentially offset from the infusion port 25. In another embodiment illustrated in FIG. 6, the infusion port 25 forms an opening in the inner sidewall of the hub 20 as discussed above, and the collection port 27 forms an opening at the proximal end 23 of the hub 20 and axially aligned with the catheter 11. Like the hub 20, the catheter 11, infusion port 25, infusion tube 26, collection port 27 and collection tube 28 are preferably formed of a clear material so that the infused fluid and collected composition can be seen in the catheter 11, hub 20 and both tubes 26, 28.

The tubes 26 and 28 can include fluid flow controls to adjust or prevent the fluid flow in the hub 20 and the catheter 11. These controls can include, but are not limited to, stopcocks, valves, pressure clips or other control members that are capable of closing or opening a respective tube 26, 28 or the catheter 11. These controls (valves or stopcocks) are capable of operating independent of each other, e.g. so that the fluid flow in the tubes 26, 28 can be separately controlled. Thus, patterns of control of the fluid flow in a lavage procedure of a breast duct can include, e.g. an open infusion tube when the collection tube is closed, an open infusion tube when the collection tube is open, a closed infusion tube when the collection tube is open, and a closed infusion tube and when the collection tube is closed. Additionally, the tubes 26, 28 may be compressible or pinchable with fingers or clamps or other pinching or compressing mechanism so that a practitioner can manually stop the fluid flow within each of the tubes 26, 28 when desired.

The distal end 21 of the hub 20 or the connecting conduit section can contact the outer surface of the nipple and act as a stop 29 for preventing the catheter 11 from penetrating deeper into the breast duct 130 than intended. Alternatively, the catheter 11 could have a shoulder or other enlargement that contacts the nipple or other portion of the body and acts as a stop 29 to prevent the further introduction of the catheter 11 and the further penetration of its end 12 beyond a predetermined lavaging position, such as the first branch of the breast duct or another lavaging position deeper within the duct 130. The phrase "lavaging position" as used herein describes a location, in a breast duct between the ductal sphincter and the first ductal branch or the first ductal branch that is intended to be lavaged. This position can be predetermined by measurements or determined based on feel during introduction. For example, if the branch to be lavaged is proximal the first ductal branch within the breast, the lavaging position will be achieved when the catheter 11 is positioned by the shoulder/stop 29 so that its distal end 12 is proximate the first branch to be lavaged and in between the distal branches that are not being ravaged and the first branch being lavaged.

In another embodiment as shown in FIG. 3, the device 10 could include a collar located, applied or built onto the external portion of the catheter 11 to act as the stop 29 and prevent penetration beyond the distance from end 12 to the collar so that a predetermined depth is achieved within the duct 130 and the proper lavaging position is achieved, for example beyond the first ductal branch. The stop 29, shown in FIG. 3, can be slid or otherwise adjustably retained on the catheter 11 so that different lavaging positions are achieved. Additionally, the catheter 11 may have markings on its sidewall that indicate the penetration depth of the distal end 12 of the catheter 11 into the duct 130. In a preferred embodiment, the stop 29 can be slid along the length of the catheter 11 to the position that corresponds to the depth within the breast that the practitioner wishes to advance the catheter 11—the lavaging position. When this lavaging position has been reached, the stop 29 is secured in place on the catheter 11 so that the catheter 11 cannot be further advanced into the breast duct 130 after the stop 29 contacts the nipple. Since the stop 29 can be adjustably positioned along the length of the catheter 11, the effective length of the catheter 11 within the duct can be varied so that the distal end 12 of the catheter 11 is located at any desired lavaging position within the duct.

In any of the above-discussed embodiments, the stop 29 may contact the nipple, another portion of the patient's body or an artificial structure adjacent the patient (not shown). The height of the artificial structure may be adjustably set for each individual patient.

After the distal end of the catheter 11 is positioned within the duct 130 at the ravaging position, the stop 29 will engage the nipple, adjacent body portion or the artificial structure as discussed above. When this occurs, the catheter 11 will extend past the ductal sphincter 110 so that its distal end 12 is positioned in the lactiferous sinus 120 (FIG. 1) or in the main section 132 of the duct 130 at a predetermined desired position, such as before the first branch 135 (FIG. 1). The distance the catheter 11 extends within the duct is between approximately ten and thirty millimeters. In a preferred embodiment, the working length of the catheter 11 is about fifteen millimeters, however, the length could be up to twenty-five millimeters. As discussed above, the catheter 11 can be sized so that the distal end 12 of the catheter 11 can be positioned at any point between the nipple and the first branch 135 of the duct 130 or at any point that is deeper into the duct 130 than the first branch 135. Similarly, if desired, the distal end 12 can be sized so that it could be positioned in any one of the ductal branches. No matter its location, the catheter 11 remains within the duct 130 during the procedure so that the amount of the composition needed to perform a complete cytological exam is retrieved.

The catheter 11 is formed of a material that is laterally flexible (direction at an angle to its length) so that it conforms to the path through the ductal opening, past the ductal sphincter 110 and into the lactiferous sinus 120. The catheter 11 is also longitudinally rigid to resist collapsing during its insertion into the duct 130. As a result, the catheter 11 is laterally flexible and longitudinally stiff. The catheter 11 may be composed of any biologically compatible polymeric resin(s) or metal having suitable characteristics when formed into the tubular catheter portions. Exemplary materials include polyvinyl chloride, polyethers, polyamides, polyethylenes, polycarbonate, polyurethanes, copolymers thereof and the like. The proximal portion may be formed of the same or different material as the distal portion. Optionally, all or only portions of the catheter 11 may be reinforced with a metal or polymeric braid or other conventional reinforcing layering.

As a result of the properties of the materials used to form the catheter 11, the catheter 11 is able to easily move through the nipple, past the ductal sphincter 110 and into the lactiferous sinus 120 without causing the patient discomfort. Additionally, the lateral flexibility of the catheter 11 reduces breakage and patient injury because it is able to conform to the shape of the passageway between the exterior of the nipple and the lactiferous sinus 120. The lateral flexibility of the catheter 11 may vary depending on the preferences of the user. For example, some doctors may prefer a somewhat rigid catheter 11 with only a small amount of lateral flexibility that can be quickly and easily inserted into the duct 130. The rigidity of such a catheter 11 permits its quick introduction because its strength will cause the passageway from the nipple to the lactiferous sinus 120 to conform to its shape. Conversely, other practitioners may wish to have a very flexible catheter that will conform to every bend it encounters after being positioned within the nipple. As mentioned above, the longitudinal stiffness (column strength) of the catheter 11 allows it to be advanced past the sphincter 110 and into the lactiferous sinus 120 without collapsing or otherwise deforming under pressure. Yet, at the same time, it may be more comfortable for the patient than the rigid catheter discussed above.

The catheter 11 is radially dimensioned to permit introduction of the distal end through the ductal orifice and positioning the first end 12 thereof beyond the ductal sphincter of the breast, e.g., typically having an outer access tube diameter in the range from substantially 0.010 inch to 0.10 inch, with the outer diameter at the port 19 being between about 0.010 and 0.050 inch with a preferred range being between about 0.010 and 0.030 inch. A preferred outer diameter may be about 0.025 inch. The outer diameter is smoothly tapered for the comfort of the patient. This can be accomplished by a smooth continuous taper or, alternatively, a series of small steps. The catheter 11 is preferably tapered within this range over a length from about 0.15 to 0.075 inch.

In a preferred embodiment, the sidewall of the catheter 11 is formed as thin as possible so that the outer diameter will be close to the same size as the inner diameter without effecting the ability of the catheter 11 to perform its intended function. The thin sidewall of the catheter 11 can be formed of a material, such as those discussed above, which exhibits high column strength under axial loading. The inner diameter of catheter 11 is substantially in the range of about 0.005 to 0.099 inch. It may be preferred to have an inner diameter in the range of about 0.005 to 0.047 inch, with a preferred inner diameter being about 0.022 inch.

As shown with phantom lines in FIG. 3, a guide member (dilator) 40 can be positioned within the hub 20 and the catheter 11 so that it extends from the distal end 12 of the catheter 11 for guiding and properly positioning the catheter 11 in the breast duct. The guide member 40 can have a length between about thirty-five and fifty-five millimeters, with a preferred distance being about forty-four millimeters. The guide member 40 permits the smooth introduction of the catheter 11 into the ductal orifice and into the breast duct. This smooth insertion can include dilating the ductal orifice so that the catheter 11 will be smoothly and painlessly introduced into the duct 130. The guide member 40 can include a stylet, an elongated dilator or any other type of catheter guide used to advance a catheter into a body opening, such as a guide wire. The guide member 40 can be made of metal or hard plastic and may have a tapered and/or an atraumatic tip 41 at the distal end 44 for gently probing, accessing and dilating one of the ductal orifices, see FIG. 8. In addition to guiding the catheter 11, the guide member 40 also stiffens the catheter 11 and increases its ability to be easily positioned in the duct.

Figure 6:
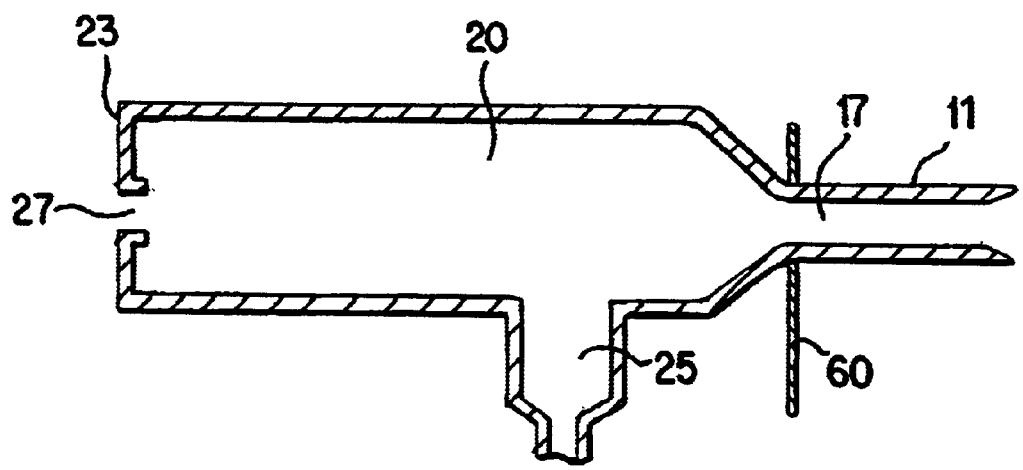

The length of the guide member 40 is chosen so that a distal end 44 will extend out of the distal end 12 of the catheter 11 and so that the taper of the guide member 40 forms a smooth transition between itself and the catheter 11. As a result, the length of the guide member 40 may depend on the length of the catheter 11, the hub 20 and any conduits extending between the catheter 11 and the hub 20. The guide member 40 tapers along its length from its proximal end 45 or a point along its length to its distal end 44. As a result, the diameter of the distal end 44 is smaller than the diameter of the proximal end 45. Ideally, the taper of the guide member 40 forms a smooth transition with the distal end 12 of the catheter 11 so that the transition is not felt by the patient as the catheter 11 is introduced into the ductal orifice. The smoother and more seamless the transition between the catheter 11 and the guide member 40, the more comfortable the procedure will be for the patient. Accordingly, the guide member 40 is sized so that its outer diameter is substantially the same or very slightly smaller by a thousandth or two of an inch as the outer diameter of the catheter 11 at the transition point between the guide member 40 and along the catheter 11. Additionally, the inner lumen 17 of the catheter 11 can have a beveled sidewall at the distal end 12 as shown in FIG. 6 so that a smooth transition will be formed between the catheter 11 and the guide member 40. The taper of the guide member 40 can end at a point along the guide member 40 that is located within the catheter 11 when the guide member 40 extends through the hub 20. After access of the duct 130 is complete, the guide member 40 can be withdrawn and the catheter 11 positioned so that its distal end 12 is beyond the ductal sphincter within the duct.

While being inserted into the hub 20 and removed from the hub 20, the guide member 40 will pass through a pneumostatic seal 42 (or the collection port 27) at a second end 23 of the hub 20 that is opposite the catheter as shown in FIGS. 3–5. When the guide member 40 is positioned in the hub 20, the seal 42 conforms to the shape of the guide member 40 to seal the hub 20 at the guide member 40 and to help support and align the guide member 40 for inserting into the catheter 11. The seal 42 also maintains the integrity of the hub 20, assists in maintaining the pressure established within the hub 20 and permits the removal of the guide member 40 after the catheter 11 has been positioned in the duct 130 prior to the infusion/collection of the lavage fluid. While many different types of seals can be used, the seal 42 should be a watertight membrane or sheath to provide a sterile environment in the hub 20 even with penetration and withdrawal of the guide member 40. The seal 42 should also provide an appropriate amount of resistance to the guide member 40 so that the guide member 40 can be manipulated into and out of the duct 130 and the catheter 11. Other types of seals that will perform similar functions can also be used.

Figure 7C:
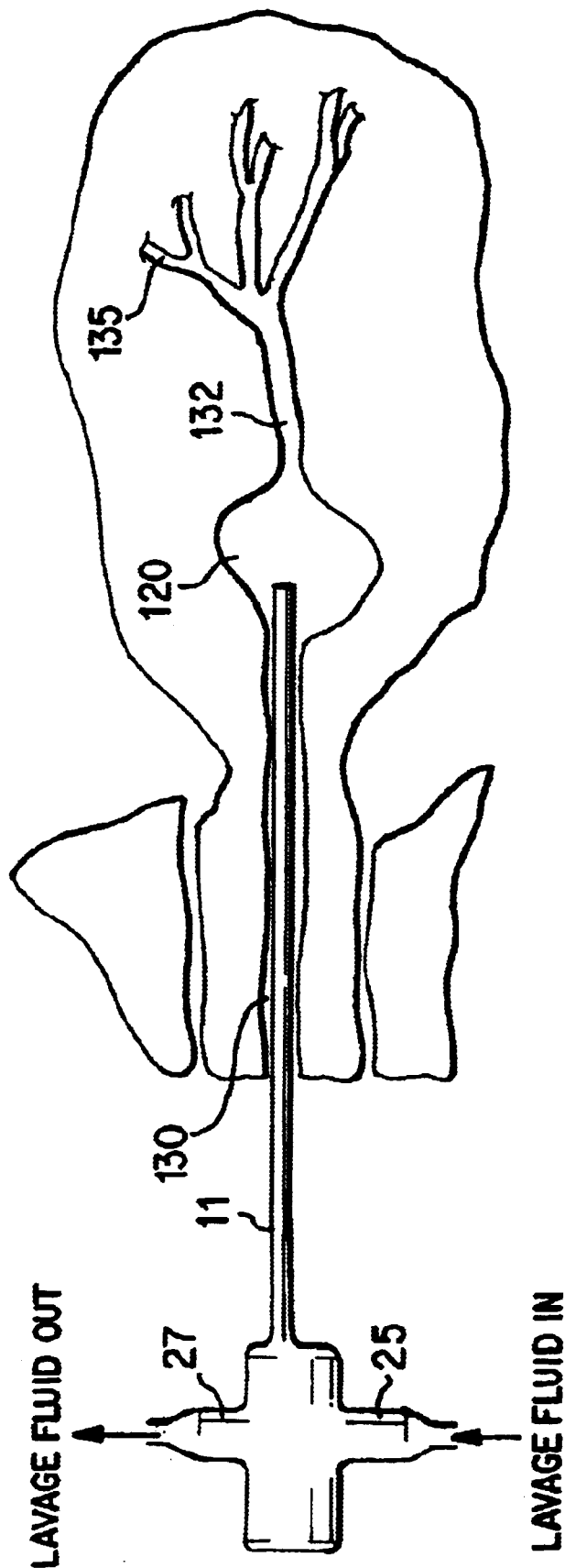
FIG. 7C illustrates a single lumen catheter accessing a breast duct having the capacity to infuse and collect fluid outside the accessed breast duct.

The following descriptions illustrate the use of device 10. However, these descriptions are equally applicable to the other devices disclosed herein. FIG. 7A depicts filling the breast duct 130 using device 10 and allowing the introduced fluid to remain in the duct 130 for a preselected time. For example, the fluid may remain in the duct 130 for one second to one or more hours. In a preferred embodiment, the fluid remains within the duct 130 for between ten seconds and ten minutes. FIG. 7B depicts removing the composition through the catheter 11 that remains in the duct 130 during and after the filling of the duct 130 and collecting of the composition including biological material from within the duct. FIG. 7C depicts the hub 20 according one embodiment of the present invention with the infusion tube 26 and the collection tube 28 positioned exterior to the accessed duct for separately infusing fluid into the duct and collecting the composition from the duct. However, as discussed above, the hub 20 could be arranged and sized so that it also extends within the duct. As understood by one of ordinary skill, the catheter 11 and the hub 20 are dimensioned to permit insertion of the catheter 11 past the ductal sphincter 110.

In any of the above-discussed embodiments, the infusion and collection tubes 26, 28 can include the above-discussed stopcocks or valves for controlling the flow of the lavage fluid into and out of the hub 20. Additionally, as discussed above, the syringe 78 can be inserted in the end of the infusion tube 26 for infusing the lavage fluid into the duct. The syringe 79 can also be inserted into the end of the collection tube 26 for creating an area of low pressure in the collection tube 28 and at least part of the hub 20 for retrieving the composition as discussed below.

During the procedure of injecting the lavage fluid into the breast duct 130 and retrieving the composition, it is important that the access device 10 not slip out of the duct. Hence, an anchor 60, shown in FIG. 6, can be attached to the catheter 11, the hub 20 and/or another portion of the access device 10 that is external the duct 130 for limiting the movement of the access device 10 relative to the nipple and possibly preventing the distal tip 12 from going beyond the lavaging position. The anchor 60, also referred to as a stop, can prevent movement of the device 10 in a direction parallel to the length of the catheter 11 or in a direction at an angle to the length of the catheter 11 (lateral motion). The anchor 60 can include an elongated member, such as a medical or body tape, having at least one side carrying an adhesive. As a result, the anchor 60 can affix, strap, tether, tape, or otherwise anchor the device 10 to the breast during the procedure in order to ensure that the device does not slip out of the duct. Such anchoring also provides the practitioner with better control of the device and eliminates the need for the device 10 to be held by the practitioner or an assistant. Additionally, reducing the amount of motion experienced by the device 20 will increase the comfort of the patient, free the practitioner's hands, reduce the work required of the practitioner and reduce the number of hands that are needed in the area of the nipple at any one time.

In a preferred embodiment, a first end of the anchor 60 can be attached to the catheter 11 or hub 20 using any known connection, such as an opening in the anchor 60 that receives the catheter 11 or hub 20. A lower surface of the anchor 60 includes an adhesive for securing the remainder, or a portion of the remainder, of the anchor 60 to the patient. Alternatively, the lower surface could include a cohesive that permits the anchor 60 to be securely attached to a member carrying the cohesive that is already secured to the body, such as a member attached to the patient to carry the nipple cover disclosed in co-pending U.S. patent application Ser. No. 09/793,110. The cohesive reduces the probability that the anchor 60 will stick to the practitioner or to itself during application. In any of the above-discussed embodiments, the anchor 60 can include a release layer that is separated from the lower surface of the anchor 60 in order to expose the adhesive/cohesive. Although the anchor 60 is disclosed to include a strip of material having a lower surface covered with an adhesive or a cohesive, any known manner of securing a lumen to a body may also be used.

One or more members positioned within the duct may also prevent premature movement or removal of the catheter 11. For example, the first end 12 of the catheter 11 can be anchored once it passes the ductal sphincter by the following steps: (1) placing the first end 12 to a depth within the duct beyond the ductal sphincter and (2) setting an anchor. The step of setting the anchor includes inflating a balloon (not shown) that will act as a stop 29 and hold the device 10 below the ductal sphincter during the infusion and collection procedures.

The catheter 11 can have the distal portion of the catheter body stiffened over at least a part of its length to facilitate insertion through the ductal orifice and into the ductal lumen of the breast duct. The stiffened distal portion of the catheter body can have an average bending stiffness in the range from about 0.010 inch-lbs to about 0.5 inch-lbs. Typically the bending stiffness of the distal portion will be about 0.105 inch-lbs. The distal end 12 will typically have a hardness in a durometer range at least greater than that of the proximal end 14, and thus generally greater than 75D. The hardness of the distal end 12 may be in a range from about 70D to about 90D. The proximal end 14 will be more flexible and less stiff and also have a lower hardness than the distal end 12. The durometer of the proximal end 14 of the catheter 11 can be in a range from about 45A to about 100A, and typically about 80A. The flexibility of the proximal end 14 provides the catheter with the advantages that the distal end 12 (which is stiffer) can be inserted into the breast duct, meanwhile the proximal end 14 can connect at its hubs with infusion or collection apparatus and not kink during the placement of the distal portion in the breast duct. Additionally, the flexibility of the proximal end 14 provides the advantage that once the distal end 12 is placed in the breast duct the catheter 11 will have less of a tendency to pull out of the duct. The stiffness of the distal end 12 benefits the procedure by allowing access into the orifice of the duct and the duct 130 itself, an action that requires a probe-like quality of the distal end 12 and distal tip in order the duct 130 to be accessed successfully.

The body of the catheter 11 may further comprise other components, such as radiopaque fillers; colorants; reinforcing materials; reinforcement layers, such as braids and helical reinforcement elements; or the like. In particular it would be possible to reinforce the distal end 12 in order to enhance its duct penetration or probe-like capabilities while optionally limiting its wall thickness and outside diameter so that the catheter 11 can easily access even ducts with small ductal orifices.

As shown in FIG. 9, the catheter 11 can include an atraumatic distal tip 68. The tip 68 can be contoured and/or rounded to reduce or eliminate trauma to the nipple (for example if a dilator is not used) and duct 130 upon entry through the ductal orifice and penetration into the ductal lumen. The tip 68 may also be fashioned to reduce or eliminate trauma upon withdrawal of the tool from the duct after the lavage procedure is completed. The tip 68 can be composed of a soft polymeric material, e.g. including polyvinyl chloride, polyethers, polyamides, polyethylenes, polyurethanes, copolymers thereof and the like. The tip 68 can have a diameter in the range from about 0.012 inches (0.031 mm) to about 0.020 inches (0.051 mm), more typically a diameter in the range from about 0.014 inches (0.036 mm) to about 0.018 inches (0.046 mm). The length of the tip 68 (extending from the distal end of the main catheter body 66) can be in a range from about 0.25 cm to about 2.5 cm, more typically in the range from about 0.50 cm to about 1.8 cm.

Figure 10:
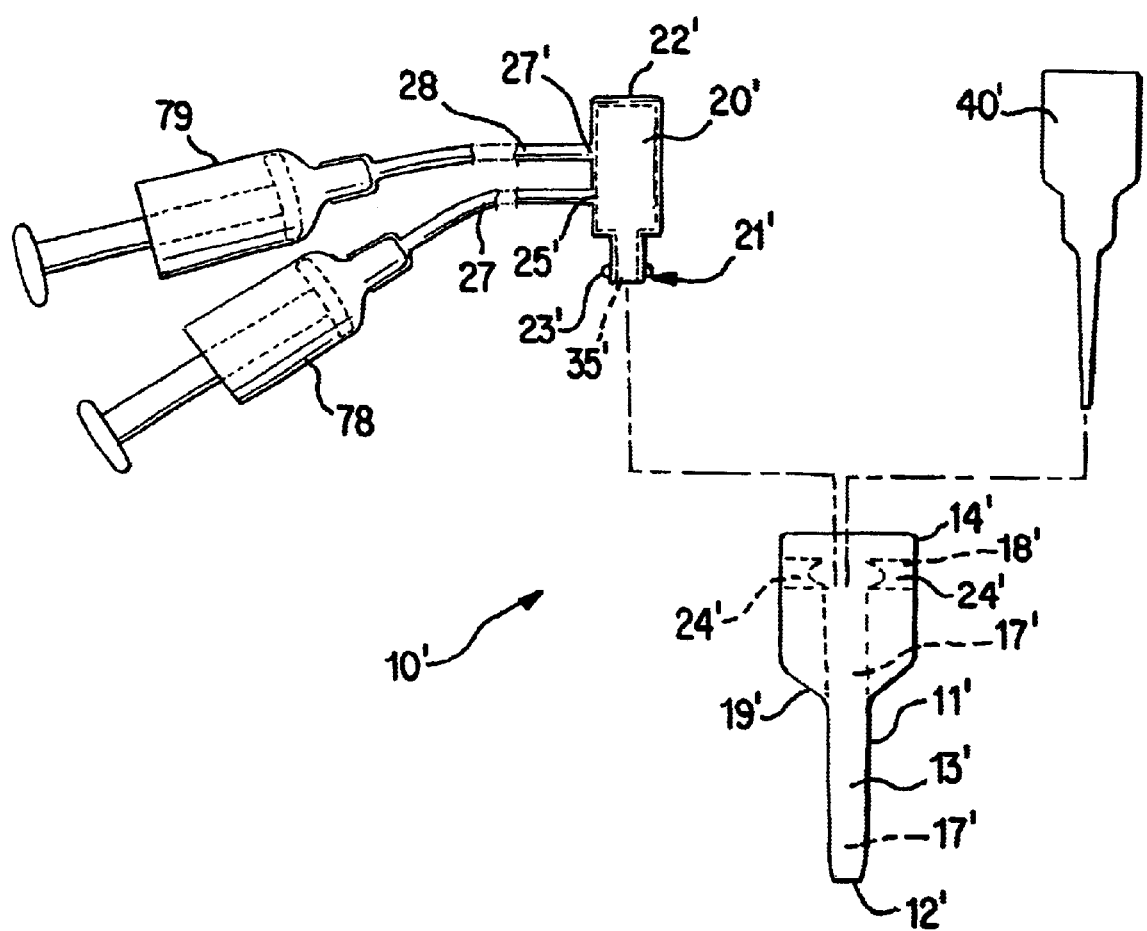
FIGS. 10–12 illustrate another embodiment of a ductal access device according to the present invention.
Figure 11:
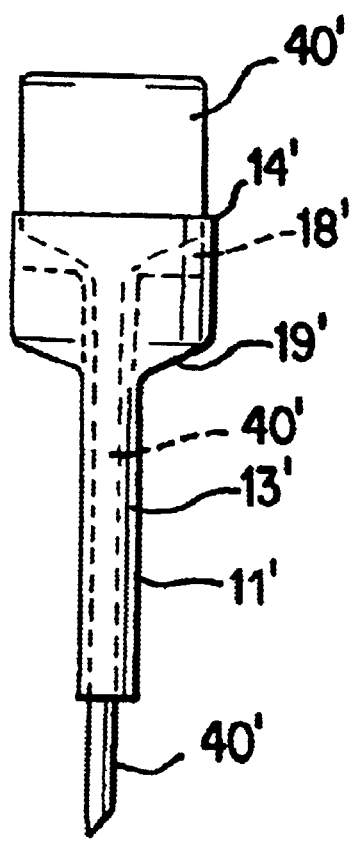
Figure 12:
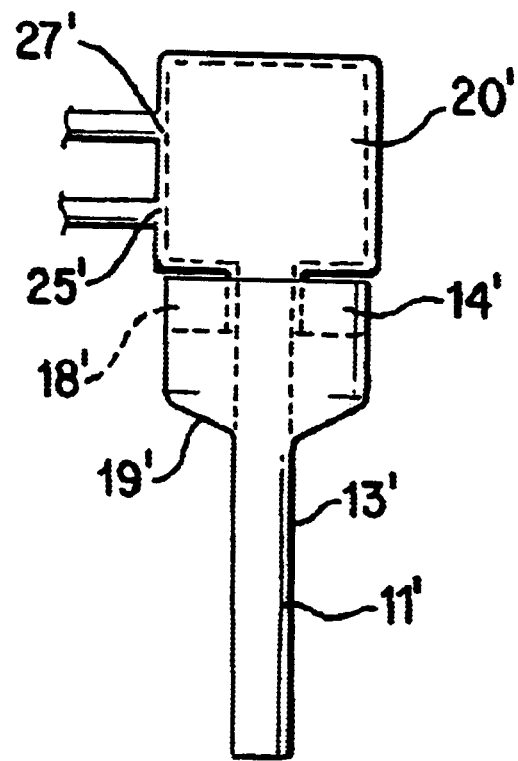

Another embodiment of the ductal access device 10' is illustrated in FIGS. 10–12. This embodiment includes an elongated accessing member (catheter) 11' having a distal end 12', a main body portion 13' and a proximal end 14'. The length of the catheter 11' is the same as those discussed above with respect to catheter 11. The distal end 12' is similar to that discussed above with respect to catheter 11 and has similar dimensions. The proximal end 14' includes a well 18' that has an outer diameter that is greater than the outer diameter of the main body portion 13'. For example, the outer diameter of the catheter 11' is about thirty to about thirty-five thousandths of an inch, and the outer diameter of the well 18' is about five to six millimeters with one-half millimeter sidewalls. A lower, outer shoulder 19' formed at the junction of the well 18' and the main body portion 13' can act as a stopper to prevent the catheter 11' from being inserted into the breast duct 130 further than intended. In one embodiment, this shoulder is about fifteen millimeters from distal end 12'. The interior of the well 18' forms a portion of the inner catheter lumen 17' that extends from the proximal end 14' to the distal end 12' for inducing fluid into the breasts and retrieving fluids and cells (cell clumps) from within the breast. The well 18' has an inner diameter of about four and one-quarter millimeters, an outer diameter of about five to five and one-half millimeters and a length of about five millimeters. As with the above-discussed embodiments, a guide member 40 or 40' (dilator) can be positioned within the catheter 11' for introducing and positioning it within the duct. Alternatively, the catheter 11' can have a distal atraumatic tip 12' that allows it to be introduced into the duct 130 without using the guide member 40, 40'.

This embodiment also includes a hub 20' that is removably secured within the well 18'. The hub 20' can be secured into the well 18' in any known manner including friction fits and interference fits. For example, the hub 20' can be secured in the well 18' by snap fitting a ridge 12 or the like within a groove 24' in the inner sidewall of the well 18' as shown in FIG. 10. In an alternative embodiment, the ridge 23' could be part of the inner sidewall and the groove 24' could be formed in the hub 20'. In the illustrated embodiment, a distal end 21' of the hub 20' is retained within the well 18' by a luer lock or friction fit. The distal end 21' of the hub 20' includes a tapered region having an outer diameter of about two millimeters that is smaller than the inner diameter of the catheter well 18' by a quarter of a millimeter or less so that a friction fit is achieved when the distal end 21' of the hub 20' is positioned within the well 18' as shown in FIG. 12. The hub 20' can have an internal diameter that is greater than that of the internal diameter of the catheter 11'.

Like the hub 20, the hub 20' includes a closed proximal end 22' that prevents fluid from escaping from within the hub 20' (as shown in FIG. 4 with respect to hub 20). Unlike the hub 20, the end 22' of hub 20' does not include a centrally positioned opening for receiving an insertable guide member 40, 40'. However, like hub 20, hub 20' includes an infusion port 25' and a collection port 27' that are the same and operate the same as infusion port 25 and collection port 27. Similarly, port 25' and port 27' can be positioned on the sidewall of the hub 20' in any of the manners and orientations discussed above with respect to hub 20. In a preferred embodiment, the hub 20' has an overall length of about twelve millimeters and the infusion port 25' is spaced from the collection port 27' by a distance of about six millimeters. The infusion port 25' is spaced from the distal end of the hub 20' by a distance of about one millimeter or less and the proximal end 22' by a distance of about ten millimeters. As a result, when the collection port 27' is located at the proximal end 22', the infusion port 25' is spaced from the collection port 27' by about ten millimeters.

In an alternative embodiment, the infusion port 25' is formed in the sidewall of the catheter 11' or the well 18'. A corresponding opening can also be formed in the sidewall of the hub 20' and aligned with the port 25' of the well 18' so that fluid introduced through the infusion port 25' enters the catheter 11' and moves into the duct 130. In this embodiment, the infusion port 25' is positioned as close to the nipple surface as possible.

Unlike the device 10 where the dilator 40' is positioned through the hub 20 and the catheter 11 in order to position the catheter 11 in the breast duct, the device 10' is positioned by first locating the catheter 11' in the duct 130 and then securing the hub 20' to the catheter 11'. In this embodiment, the dilator 40' is positioned in the catheter 11' so that its distal end 41' extends through and beyond the distal end 12' of the catheter 11' as shown in FIG. 11. The handle 42' of the dilator 40'can be located near or partially in the well 18'. After the dilator 40' is positioned in the catheter 11', the catheter 11' is introduced through the nipple and into the breast duct 130 to a desired depth where end 12' achieves a predetermined lavaging position. In one embodiment, the desired depth is distal the ductal sphincter and proximal the first branch of the duct. Once the catheter 11' is set to the desired depth, the dilator 40' is removed from the catheter 11' and the distal end 21' of the hub 20' is fitted into the well 18' while the catheter 18' is still in the duct 130 so that a fluid passageway 35'extending through the distal end 21' of the hub 20' is aligned with the lumen 17' in the catheter 11'. This creates a fluid path between the hub 20' and the catheter 11'. After the hub 20' is secured in the well 18', the device 10', including hub 20', is operated in the same manner as discussed below with respect to device 10.

Like the catheter 11 and hub 20, the well 18', alone or in combination with the hub 20', does not cause the catheter 11 to tip or fall to one side after being positioned within the duct 130. As a result, these parts of the devices 10, 10' do not torque or otherwise deform the duct 130 so that the duct 130 is twisted and/or the flow of fluid and biological material out of the duct 120 impeded.

While the following discussions are applicable to both catheter 11 and catheter 11', for ease of explanation, the discussion will be limited to catheter 11. In a first embodiment, the distal end 12 of the catheter 11 is inserted into the breast duct 130 in a closed position and then opened after it has reached a desired location, such a distal the ductal sphincter. As shown in FIG. 13, the distal end 12 of the catheter 11 is closed before it is introduced into the breast duct. When closed, the outer diameter of the distal end 12 is the same as discussed above—between about ten and thirty-five thousandths of an inch, with a preferred diameter being about thirty thousandths of an inch. In one embodiment, the outer diameter of the distal end 12 is about the same as the outer diameter of the distal end of a conventional dilator. The distal end 12 also includes openings 210 defined by sidewalls 211 that extend between the inner and outer walls of the catheter 11 as shown in FIG. 14. After the distal end 12 has been introduced into and positioned within the breast duct, the distal end 12 is opened along openings 210 by an opening mechanism 200 so that the inner lumen of the catheter 11 is open to the breast duct. The catheter 11 could be formed of any known flexible biocompatible material that includes good column strength. For example, the material could include polyethylene, high-density polyethylene, urethane or other known plastics. Alternatively, as shown in FIG. 13, the distal end 12 or all of the catheter 11 can be formed by any known, biocompatible shape memory material that will achieve an open distal end 12 in response to a stimulus such as electric current, heat or the like. In one embodiment, the shape memory material is nickel-titanium (NiTi or Nitinol).

When open, as shown in FIG. 14, the distal end 12 has an inner, open diameter of about at least twenty to twenty-five thousandths of an inch. The inner diameter of the opened distal end 12 can be greater than that of a conventional catheter because of the flexibility provided by the openings 210 on the sidewalls and the opening mechanism 200 or shape memory materials. The opening mechanism 200 and/or shape memory material can also be used to close the distal end 12 in order to trap collected cell samples and cell clumps in the catheter 11.

In a first embodiment, the opening mechanism 200 includes a wire 251 that extends through the sidewall of the catheter 11. The wire 251 has a distal end 252 connected to the distal end of the catheter 11 as shown in FIG. 14. A proximal end 253 of the wire 251 extends from the proximal end of the catheter 11 so that an operator can manipulate it. A lever or series of levers could be used in place of the wire 251. In an alternative embodiment, the opening mechanism 200 can include the guide member 40 positioned through the inner lumen of the catheter. This guide member 40 will spread open the distal end 12 of the catheter until it locks in the open position. Expandable springs with releasable tension and/or shape memory materials could also be used. A first wire 251 can stop at one side of the opening and a second wire 251 can extend across the opening along the side of the catheter as shown in FIGS. 14A–14B. The two wires can be operated separately or together for individually or simultaneously opening or closing the sides of the opening 210. The embodiment shown in these figures includes an atraumatic rounded distal end. FIG. 14C illustrates an embodiment in which the opening 210 is offset along the catheter 11 and the moving portion of the catheter is larger than the stationary portion.

In an alternative embodiment illustrated in FIGS. 15 and 16, the distal end 12 of the catheter 11 includes a main, stationary section 305 and a distal, sliding portion 310 that can be moved toward the proximal end 14 when an opening mechanism 350 is activated. As shown in FIG. 16, the sliding portion 310 is moved along the length of the catheter 11 so that its distal end 312 slides beyond the end of the non-moving portion of the catheter 11. After the sliding portion has been fully retracted, the distal end 12 includes an opening 315 that extends along the longitudinal axis of the catheter 11. The opening 315 extends along the longitudinal axis of the catheter about six to twenty-five thousandths of an inch and across the inner diameter of the catheter 11 which is about the same as discussed above for the embodiment illustrated in FIG. 1.

The opening mechanism 350 can include a wire 351 or other member that extends from the proximal end 14 to the sliding portion 310 as shown in FIG. 15. The practitioner can pull the proximal end of the wire 351 so that the sliding portion 310 of the catheter 11 moves upward along the catheter 11 in the direction of the proximal end 14. The wire 351 is then forced downward toward the distal end 12 when the sliding portion 310 is intended to be in the closed position, such as before the catheter is inserted into the breast duct 130 and in preparation for removing the catheter 11 from the breast.

In another embodiment, the catheter 11 is similar to that illustrated in FIG. 15. However, instead of including a single sliding portion, the proximal end 12 includes a pair of sliding portions 305, 310. Similarly, the opening mechanism 350 includes two wires 351 as shown. The first wire 351 moves the first sliding portion 310 when it is moved toward the proximal end 14 or the distal end 12. The second wire 351 moves the second sliding portion 310 in a similar manner to the first sliding portion 310. When both of these sliding portions 310 are in an open position, such as when the catheter 11 is positioned within a breast duct, the diameter of the opening 355 of the catheter 11 is between about six to twenty-five thousandths of an inch. In preferred embodiments, the inner diameter is about twenty or twenty-five thousandths of an inch.

FIG. 17 illustrates an additional embodiment of the present invention. In this embodiment, the sliding portion 310 moves downward and away from the distal end of the catheter 11. As the sliding portion 310 moves downward under the influence of the opening mechanism 350, it can also move away from the remainder of the distal end 12 of the catheter 11 so that an opening 359 is formed at the distal end 12 for collecting samples (cell clumps, fluids, etc.) from within the duct. Also, the sliding member 310 can be used to trap samples within the catheter 11. In operation, the closed catheter 11 is introduced into and seated in the breast duct. Next, the sliding member 310 is opened using the wire or linkage 351 of the opening system 350. Once the distal end 12 of the catheter 11 is open, lavage fluid is introduced into the breast duct. The samples can be collected in the open distal end 12 using external pressure applied to the breast while it is being massaged or negative pressure applied to the proximal end 14 of the catheter 11. Retracting the wire or linkage 351 closes the distal end 12 of catheter 11.

In another embodiment shown in FIG. 18, the distal end 12 includes a beveled surface portion 410 and a rounded end portion 420. The beveled surface portion 410 extends from a longitudinal sidewall of the catheter to the rounded end portion 420. The beveled surface portion 410 includes the opening to the inner lumen 17 of the catheter 11 that extends at an angle to the longitudinal axis of the catheter 11. As a result of the angle of the beveled surface portion 410, the opening to the lumen 17 can be directed at a ductal branch for easy and direct introduction of fluids into a branch, especially an angled branch. The orientation of the lumen 17 opening can also make collection of samples from these branches easier. Moreover, the opening can be larger than traditional openings to catheter lumens so that collection is easier and more efficient. The angle of the beveled surface is between about thirty and sixty degrees, with preferred angles being about forty degrees and forty-five degrees. As seen in FIG. 18, the rounded end portion 420 forms a bulbous tip at the distal end 12 that extends from the outer sidewall of the catheter 11 to the distal most portion 412 of the angled surface 414 of the beveled surface portion 410. The rounded end portion 420 eliminates any sharp edges at the distal end 12 and permits the smooth introduction of the catheter 11 into the duct.

Figure 22:
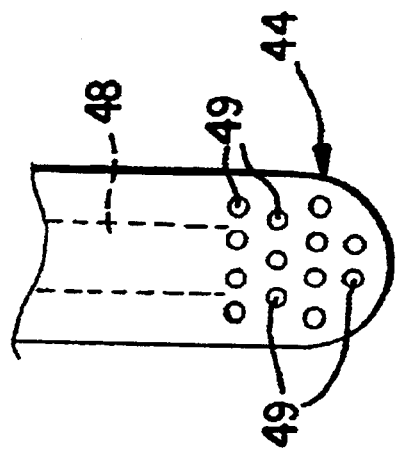
Figure 19:
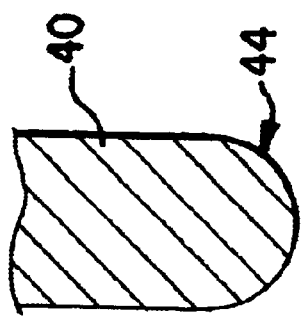

The following discussions are equally applicable to both catheter 11 and catheter 11'. However, for clarity of explanation, the discussion will focus only on catheter 11. The guide member 40 can be a conventional dilator having a solid cross section at its distal end 44 as shown in FIG. 19. Alternatively, the guide member can include one of the distal ends illustrated in FIGS. 20–22. Each of these illustrated distal ends 44 has at least a portion that is hollow so that it can carry and/or deliver a medicament to the nipple, the ductal lining and/or the sphincter. The medicaments include any of the above-mentioned medicaments including lubricants, topical anesthetics and antibiotics. One medicament that can be carried by the distal end is lidocaine.

Figure 20:
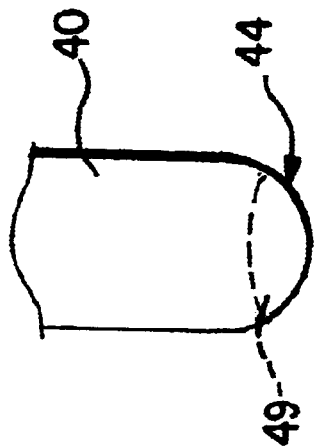
FIGS. 19–22 illustrate different distal ends for a ductal dilator.
Figure 21:
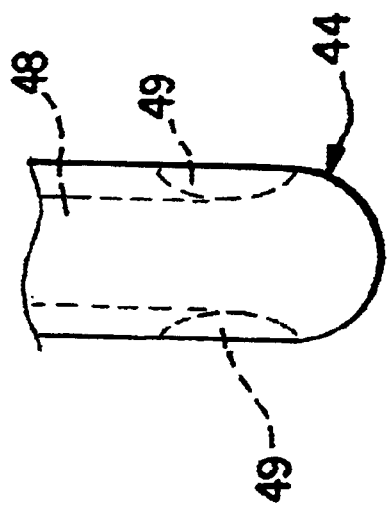

The catheter tip illustrated in FIG. 20 includes a plurality of openings 49 spaced around the circumference of the dilator 40. The openings 49 extend along the dilator 40 so that their major axis is perpendicular to the longitudinal axis of the dilator. These openings 49 can also narrow as they approach the distal end 44 of the dilator 40. The openings 49 carry a predetermined amount of a medicament that is applied to the nipple, ductal lining or sphincter as the dilator is introduced and positioned in the duct. In the embodiment illustrated in FIG. 21, the major axis of the openings extends parallel to the longitudinal axis of the dilator 40. In the embodiment illustrated in FIG. 22, the distal end 44 includes a plurality of smaller openings positioned around the distal end 44 in a random or predetermined pattern. In any of the above-discussed embodiments, the medicament is provided in the openings 49 by dipping the distal end 44 in the medicament. In an alternative embodiment, the medicament is introduced to the openings 49 in the distal end 44 through an internal lumen 48 that is open at a proximal end of the dilator 40. The proximal end of the dilator 40 can receive a medicament introduction system that introduces the medicament into a proximal end of the inner lumen 48. The medicament then flows through the lumen 48, out the openings 49 and into contact with the ductal lining. In one embodiment, the introduction system includes a syringe or other known medicament introducing members. These medicament introduction openings are not limited in use to the guide member 40. Instead, they can also be provided to the distal end of any of the above-mentioned catheters 11, 11'.

In the exemplary embodiment, the distal and proximal portions of the catheters 11, 11' and/or the dilators 40, 40' can be coextruded. The coextrusion process can generate the intermediate zone in accommodating the differential cross-sectional geometry of the proximal to the distal portions.

The invention also provides systems and kits for collecting cellular material from a breast duct. The system comprises any of the above discussed access devices 10, 10', a premeasured solution to infuse into the duct (optional), instructions for use of the catheter and lavage fluid to access a breast duct and retrieve the composition and, optionally, any one or a combination of the agents discussed in U.S. patent application Ser. No. 09/473,510. It is possible to use any of the above-discussed embodiments of the access device 10 with the system. The instructions can set forth any of the methods described herein, such as the method for obtaining the composition from a human breast milk duct comprising introducing the provided ductal access device 10 having an at least one lumen catheter 11 into a breast duct, introducing a lavage fluid through the catheter 11 into the duct, wherein a volume of at least 2 ml is present within the duct for a preselected time; and collecting at least a portion of the composition in the duct after the breast has been massaged through the lumen of the access device.

The lavage fluid used with any of the above discussed access devices 10, 10' or the methods discussed below can be any of those disclosed in U.S. patent application Ser. No. 09/473,510, which has previously incorporated by reference. For example, the kit 60 could include saline, phosphate buffered saline, a nonabsorbable fluid, an isotonic solution, an osmotic solution, a hypotonic solution, a hypertonic solution, a protein, a colloid, a sugar, a polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, a synthetic colloid, an antibody, a binding protein, albumin or any other lavage fluid discussed herein or that is known in the art. Additionally, the lavage fluid could include any of the agents discussed in U.S. patent application Ser. No. 09/473,510.

As discussed above, the present invention also includes a method for lavaging a breast duct. This method generally includes the steps of introducing any one of the above discussed ductal access devices 10, 10' into the breast duct 130, locating the first end 12 of the catheter 11, 11' at a desired position within the duct 130, introducing a lavage fluid into the duct 130 for washing the duct 130, retrieving a composition from the breast that includes cellular material from the duct and collecting the retrieved composition for cytological examination. For clarity, the method according to the present invention will be discussed as it relates to device 10. However, this discussion is completely applicable to the device 10'.

At the beginning of the procedure, a ductal access patient's nipple is cleaned with alcohol, and dekeratinized with cerumetix. An aspiration cup is then placed on the nipple and areola and the patient's nipple is aspirated to identify the breast duct yielding the fluid. The duct(s) that yields the fluid is (are) then accessed using one of the above-discussed dilators that extend from one of the above-discussed catheters.

The method also includes the step of preparing the device 10 including the catheter 11 for introducing into the breast duct through the ductal opening. The practitioner can determine the depth that the catheter 11 needs to be inserted into the duct 130 prior to inserting the catheter 11 into the duct 130 or after the catheter 11 has been inserted into the duct 130 so that the desired lavaging position is achieved. If the practitioner does determine the depth for insertion, the stop 29 can be used to establish the desired positioning of the distal end 12 in the ductal network. Alternatively, the practitioner can use presized devices 10 that include stops in predetermined locations that stop the insertion of the catheter 11 at a predetermined depth.

The practitioner will then obtain a dilator 40 and position it within the hub 20 and the catheter 11 (or just the catheter as discussed above). During this step, the practitioner can determine the size of the dilator 40 that needs to be used to dilate the ductal orifice to the proper size. Alternatively, the dilator 40 can already be positioned within the hub 20 and the catheter 11 of a device 10. In this instance, the practitioner will select the device 10 that meets the size requirements—length and outer diameter—needed for a particular patient. After the dilator 40 is securely positioned within the catheter 11, the dilator 40 and catheter are advanced into the ductal orifice, past the ductal sphincter 110 and into the lactiferous sinus 120 and/or the opening to the main trunk 132 of the duct 130 before the first branch 135. However, as discussed above, the catheter 11 could be advanced so that its end 12 is positioned at any point within the duct 130 or the braches of the duct. Once the catheter is properly seated within the duct 130, the anchor 60 (if provided) can be applied to the body or other secured member for holding the device 10 in the position intended by the practitioner. Additionally, the dilator 40 can be withdrawn from the catheter 11 after the catheter 11 is comfortably seated within the breast duct 130.

As discussed above, the syringes 78, 79 can be connected to the infusion tube 26 and the collection tube 28 before or after the catheter 11 has been positioned within the duct 130. The method includes introducing a volume of between 10 ml and 25 ml of lavage fluid into the duct 130 until resistance is felt in the infusion syringe. The assumption made at that point is that the duct is filled with the infusion fluid. This step is also referred to as priming the system. After the duct has been filled, the infusion tube 26 is closed and the collection tube 28 is opened.

A volume of at least 2 ml is allowed to remain in the duct 130 for a preselected time that can range from less than or about one second to about an hour, including any length of time in between. During the time that the lavage fluid remains in the breast duct 130, it may mix with the ductal fluid already present in the duct 130 in response to externally applied breast massaging. The breast is massaged, preferably from the bottom, and then squeezed. Since the fluid within the duct 130 may accumulate cellular material either from the ductal walls or that is already present in the existing resident ductal fluid, a cloudy fluid from within the accessed duct is thus caused to enter the clear or partially clear hub 20 and begin to exit the hub through the collection tube 28. To encourage the fluid to exit, the infusion tube 26 is opened and additional infusion fluid is forced into the hub 20, causing more cloudy fluid to exit through the collection tube 28. Before or between the collection steps, the duct 130 may be refilled with the lavage fluid. For example, the lavage fluid may be infused into the duct 130 until a point of resistance to infusion is again felt, at which point it may be considered that the breast duct is once again filled with lavage fluid, and the just infused fluid can be allowed to reside in the duct for a preselected time.

Where a manifold hub 20 is present in the access device 10, once the lavage fluid mixes with ductal fluid and cellular material is passed out of the duct 130 and into the hub 20, collection may be facilitated from the collection tube 28 without risk of collapsing the ductal wall by creating low (negative) pressure in the collection tube 28 (e.g. using a syringe and pulling back to collect material into the syringe). Additionally, or alternatively, as discussed above, the hub 20 filled with collected material may be flushed into the collection tube 28 using an infusion of lavage fluid from the infusion tube 26. The fluid flow into and out of the infusion and collection tubes 26, 28 may be controlled as discussed above.

During the introduction of the lavage fluid into the duct 130, the practitioner can either (1) introduce the lavage fluid until the breast duct is filled and then massage and squeeze the breast to help mix the fluids, or (2) fill the duct in stages while massaging and squeezing the breast in between each filling stage. Massaging and squeezing the breast in an upward direction from its base may facilitate collection of the infused fluid and the mixture of ductal fluid, lavage fluid and cellular material. The actions of massaging and squeezing the breast may also provide some disruption of the cells on the ductal walls, thereby increasing a yield of cellular material from the procedure. Obtaining the mixture with a collection lumen can be further facilitated in some cases with aspiration applied into the hub 20 or the lumen 17.

The total amount of the infused lavage fluid within the duct 130 will depend on the size of the duct. For example, larger breasts may have larger ducts that will accept more of the lavage fluid than a smaller breast with smaller ducts. The volume of infused lavage fluid can range from about 10 ml to about 50 ml or greater, with many ducts accepting 12 ml to 25 ml. Since the amount of fluid will vary with the size of the duct, a duct is usually considered full when the person introducing the fluid through the device 10 feels a significant level of resistance. The lavage fluid can be incrementally introduced into the duct.

Once the preselected amount of time for retaining the lavage fluid within the duct 130 has elapsed, the infused fluid and the contents of the duct with which it has mixed are collected. If the ductal access device 10 is used to access the duct 130 and infuse the fluid into the duct 130, the in-dwelling catheter 11 remains in the duct 130 to collect the mixed fluid and duct contents. As discussed above, a preferred embodiment of the present invention is to use the above-described single lumen catheter 11 for accessing the duct and obtaining the mixed fluids and duct contents. However, it is also possible to use one of the double lumen devices described in U.S. patent application Ser. No. 09/473, 510, which has been previously incorporated by reference. Also, as mentioned above, no matter which catheter is used, the catheter remains in place in the duct 130 during the infusion, preselected waiting time (e.g. less than one second or about one second to one hour), and collection of the lavage fluid mixed with ductal fluid and cellular material from the breast duct.

The method permits a single duct to be accessed and the cellular material from the duct to be obtained without allowing the cellular material or ductal fluid from the accessed duct to contact the cellular material or ductal fluid of any other duct, or cellular material or ductal fluid that happens to be residing on the nipple surface. This prevents the contamination of fluids from separate ducts, and thereby provides the opportunity to analyze a single individual breast duct separate from other breast ducts of the patient. Accessing a single breast duct also provides the opportunity to collect ductal fluid and cellular material from the chosen breast duct separate from other ducts in the breast, without mixing or contacting the collected fluids and cellular material with that of the other ducts. This, in turn, provides the opportunity to analyze the condition of the accessed duct separately.

Modifications to the method of lavage can include that the patient is seated during the lavage procedure, rather than the standard or classic supine (face up) position. In addition, the patient may be lavaged in a prone position, face down, with nipples and breast down. The prone face down position takes advantage of gravity and allows the breast ducts to drain into the collection receptacle during the procedure when the outflow port is open. Thus, the lavaging procedure can include infusing the breast duct with a lavage fluid through an open inflow lumen while an outflow lumen is closed; closing the inflow lumen when the duct is filled; squeezing or massaging the breast from the bottom of the breast or both; and opening the outflow lumen to collect the lavage fluid.

The lavage fluid that is introduced into the duct can comprise any biocompatible agent or solution. Thus, the lavage fluid can comprise e.g. saline, phosphate buffered saline. Additionally or alternatively, the lavage fluid can comprise an agent or agents or solution that reduces the ability of the fluid or agent to diffuse through the ductal wall or otherwise leave the duct and enter other parts of the body. Accordingly, the lavage fluid may comprise a nonabsorbable fluid, an isotonic solution, an osmotic solution, a hypotonic solution or a hypertonic solution. Fluid or agents may be administered to the breast duct in order to facilitate, increase, and/or optimize the amount of material obtained or obtainable from the breast duct during the procedure. Agents or solutions that may comprise the infused lavage fluid can include, e.g. protein, colloid, sugar, polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, albumin, a synthetic colloid, an antibody or part of an antibody, or a binding protein.

Once the lavage fluid had been infused in the duct and the lavage fluid and ductal fluid is collected from a breast duct, the cellular material can be separated and can be examined. Fluid collected from the milk ducts, can include constituents of biological fluids, e.g. those typically found in breast duct fluid, e.g. water, cells, cellular markers, molecular markers, nucleic acids, proteins, cellular debris, salts, or organic molecules. These constituents can be analyzed by any appropriate method depending on the practitioner's purposes in obtaining the fluid.

The fluid can comprise molecular and cellular materials including e.g. ductal epithelial cells and abnormal cells. Specifically, the cellular material can include, e.g. substances selected from the group consisting of whole cells, cellular debris, proteins, nucleic acids, polypeptides, glycoproteins, lipids, fats, glycoproteins, small organic molecules, metabolites, and macromolecules. Analysis of the ductal epithelial cells and/or the molecular and cellular material in the ductal fluid can proceed as described in U.S. patent application Ser. No. 09/473,510. Whole cells can be examined by cytology, or any other suitable method for analyzing the condition of the cells. The cells can be analyzed for cellular, protein, nucleic acid, or other molecular prognostic information for an evaluation of the condition of the breast or breast ducts. Removal of cells can be conducted in the presence of the agent, and preferably the action of the osmotic and/or oncotic agent provides for removing cells that can be analyzed.

The retrieved fluid can further comprise constituents of the breast milk duct fluid, e.g. including water, cellular markers, molecular markers, nucleic acids, proteins, cellular debris, salts, or organic molecules. Analyses can be made that identify molecular or cellular markers, cellular characteristics, e.g. by cytology, and for making any other assessment of any of the constituents of the fluid.

Conditions in a breast milk duct that are desirable to diagnose include a cancer or precancer condition. The precancer condition can include atypical ductal hyperplasia (ADH) or low grade ductal carcinoma in situ (LG-DCIS). The diagnostic agent may also have the ability to diagnose other breast related conditions, including, e.g. fibrotic, cystic or conditions relating to lactation.

Diagnostic agents can be mixed with the ductal fluid (either in the lavage procedure, or after the fluid is collected). Other markers present in the cellular material, ductal fluid generally, or other material obtained from the breast duct can be analyzed as is appropriate for the marker being sought, including e.g. binding assays, immunohistochemistry, or using other analytical technology for distinguishing and identifying biological molecules obtained from biological material.

The diagnostic agents can include tags for detecting lesions or other abnormalities or characteristic anatomical or molecular identities in the breast ducts, including e.g. chemical tags or antibodies. The tags may provide the capacity for visualizing the location of a lesion, including, e.g. fluorescent tags, or biotinylated tags. Antibodies can also be tagged so that the binding antibody is identifiable. Antibodies can be whole antibodies, or parts of antibodies including, e.g. Fab fragments, heavy and/or light chain fragments, single chain antibodies and other modified antibodies commonly known about and used in the field of antibody-assisted diagnosis. Diagnostic antibodies or other tags can be to a number of markers.

As understood, the cellular material is analyzed for the presence of soluble factors or other components that might indicate the presence of cancerous or precancerous ductal epithelial cells in the duct. The epithelial cells retrieved from the breast duct can be analyzed for protein markers, nucleic acid markers, chromosomal abnormalities, or other characteristic changes that would signal the presence of cancerous or precancerous cells. In addition, other cells found in the duct can also be analyzed, e.g. for an increase or decrease in these cells as compared to normal ductal fluid, or for qualities of these cells themselves. Thus, the condition of the breast duct can be analyzed e.g. for soluble protein content or presence of other ductal fluid components, including also secreted products of ductal epithelial cells) or the ductal epithelial cells themselves can be analyzed, for example, for cell morphology, for protein markers, for nucleic acid markers, and for biochemical markers.

In addition, any of the cells of the duct can be analyzed for morphological abnormalities in cell components, including, e.g. morphological abnormalities of the nucleus, cytoplasm, Golgi apparatus or other parts of a cell. Cell morphology can serve to establish whether the ductal epithelial cells are normal (i.e. not precancerous or cancerous or having another noncancerous abnormality), precancerous (i.e. comprising hyperplasia, atypical ductal hyperplasia (ADH) or low grade ductal carcinoma in situ (LG-DCIS)) or cancerous (i.e. comprising high grade ductal carcinoma in situ (HG-DCIS), or invasive carcinoma).

Analysis of cell contents may serve to establish similar staging as established by morphology, capturing generally a progression of a precancerous or cancerous condition in the cells. The cells can be analyzed for whether they do or don't aggregate (e.g. in clumps) or by making comparisons of the ductal epithelial cells with other cell types retrieved in the ductal fluid (e.g. macrophages, lymphocytes, foam cells and other possible components of ductal fluid). The ductal epithelial cells can be analyzed for their molecular contents or the morphology of the ductal epithelial cells, including, e.g. protein markers, nucleic acid markers, biochemical markers in the cells or on the cell surfaces or for any evidence of neoplasia.

Chromosomal abnormalities in ductal epithelial cells can also provide information and act as a marker to identify cancer or precancer as is known. Many known breast cancer markers are discussed and described in readily available medical textbooks on breast cancer.

Administering fluid to the ductal lumen for the purpose of collecting that fluid mixed with the fluid from the duct is complicated by the fact that absorbable lavage fluids are partly absorbed into the breast from the duct. Thus, the fluid retrieved is less than that infused, even considering that it includes the ductal fluid that was residing in the duct. Administering an agent in the lavage fluid that is capable of increasing or maintaining the fluid volume in the duct is a great advantage to the process. Thus, the invention provides administering a nonabsorbable fluid or a fluid that actually draws fluid to it, e.g. an oncotic or osmotic fluid in the process of collecting fluid from the duct. Administering the nonabsorbable fluid has the advantage also of providing the practitioner with a way to monitor or standardize the ductal fluid and cellular return in any given volume of fluid infused and retrieved. For example 10 ml of the nonabsorbable fluid is administered to the duct, and 9.5 ml of that fluid is collected. Maybe 100 epithelial clusters are contained in the fluid collected. This information can be noted, and during future procedures on that same duct can be compared. The advantage of using a nonabsorbable is that the ductal fluid yield may be increased with the retrieval of most or all of the infused fluid, and the practitioner will be able to keep track of the amount infused versus the amount collected.

A nonabsorbable fluid can be used in order to provide a standardization to the process so that the amount infused can be correlated with the amount collected, knowing that since the fluid cannot be absorbed in the duct, and collecting of all or most of the fluid that is infused is possible. Other agents that can be used to increase the amount of collectable fluid in the ductal lumen can also be used with the present invention. Examples of these agents are disclosed in co-pending U.S. patent application Ser. No. 09/473,510.

The various features of the catheters described above can serve to facilitate the practice of the lavage procedure. For example, the narrow distal tip provides the catheter the ability to penetrate the ductal orifice and move the catheter into the ductal lumen for performing the lavage procedure; the larger diameter of the proximal portion inhibits the catheter from passing too deeply into the duct, and stops the penetration of the catheter at the place where the distal portion ends and the proximal portion begins; the atraumatic tip provides the catheter the ability to penetrate the duct without trauma to the tissue walls of the ductal lumen; the stiffening material placed in at least a part of the distal portion of the catheter (e.g. a stiffening wire or a supporting braid or the like) provides the practitioner with stiffness to better control the entry and further penetration of the catheter into the ductal lumen; the ports on the lumens provide the catheter the ability to infuse liquid into the duct from the infusion lumen and the ability to aspirate or collect fluid from the duct into the aspiration lumen.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is also contemplated that the catheter could include multiple, concentrically positioned or adjacently positioned lumens that open in opposite directions. Additionally, contrast fluids can be used as the ravaging fluid.

What is claimed is:

1. A device for accessing a mammalian duct and collecting cellular material from within the duct, said device comprising:
   a catheter for being positioned within the duct, said catheter having a proximal end and a distal end, said distal end including an opening for delivering lavage fluid within the duct and receiving cellular material from within the duct; and
   a manifold hub in fluid communication with the catheter, said manifold hub comprising a distal end having a first port that is axially aligned with an internal lumen of the catheter, an infusion port positioned within the manifold hub for infusing fluids into said manifold hub and a collection port positioned within the manifold hub and being in fluid communication with said infusion port within said manifold hub, said collection port for collecting fluid received within the manifold hub, wherein said infusion port and said collection port are in fluid communication with said opening of said distal end of said catheter.

2. The device according to claim 1 wherein said manifold hub includes at least one sidewall that extends parallel to a longitudinal axis of the device, said at least one sidewall includes the infusion port and the collection port.

3. The device according to claim 2 wherein said infusion port and collection port are aligned with each other along the at least one sidewall of the hub.

4. The device according to claim 3 wherein the infusion port is positioned proximate the first port relative to said collection port.

5. The device according to claim 3 wherein the collection port is positioned between the infusion port and a proximal end of the hub.

6. The device according to claim 2 wherein said hub has a substantially circular cross section, and said infusion port and collection port are circumferentially spaced from each other around the hub.

7. The device according to claim 1 further including an infusion line connected to the infusion port and a collection line connected to the collection port.

8. The device according to claim 7 further including a fluid infusing member removably secured to a terminal end of the infusion line for delivering fluid to the infusion line and the hub.

9. The device according to claim 8 wherein said infusing member comprises a syringe.

10. The device according to claim 7 further including a collecting member removably secured to a terminal end of the collection line.

11. The device according to claim 10 wherein said collecting member comprises syringe.

12. The device according to claim 1 wherein the distal end of the manifold hub is removably secured to the catheter such that said manifold hub can be repeatedly secured to said catheter and repeatedly separated from said catheter.

13. The device according to claim 12 wherein the distal end of the manifold hub forms a luer lock connection with the catheter.

14. A device for accessing a mammalian duct and collecting cellular material from within the duct, said device comprising:

a catheter for being positioned within the duct, said catheter having a proximal end and a distal end, said distal end including an opening for delivering lavage fluid within the duct and receiving cellular material from within the duct, said distal opening of the catheter being capable of moving between a closed position and an open position;

a manifold hub in fluid communication with the catheter, said manifold hub comprising a distal end having a first port that is axially aligned with an internal lumen of the catheter, a second port positioned within the hub for infusing fluids into said hub and a third port positioned within the hub for collecting fluid from within the hub.

15. The device according to claim 14 further including a mechanism for moving the distal catheter opening between the open and closed positions.

16. The device according to claim 15 wherein said mechanism includes a wire extending between the proximal and distal ends of the catheter.

17. The device according to claim 14 wherein said distal end of the catheter is formed of a shape memory material that opens in response to the application of a stimulus.

18. The device according to claim 17 wherein said stimulus includes heat or electric current.

19. The device according to claim 17 wherein said shape memory material is Nitinol.

20. The device according to claim 14 wherein the distal end has a larger opening than the proximal end of the catheter when the distal end is in the open position.

21. A device for accessing a mammalian duct and collecting cellular material from within the duct, said device comprising:

a catheter for being positioned within the duct, said catheter having a proximal end and a distal end, said distal end including an opening for delivering lavage fluid within the duct and receiving cellular material from within the duct;

a manifold hub in fluid communication with the catheter, said manifold hub comprising a distal end having a first port that is axially aligned with an internal lumen of the catheter, a second port positioned within the hub for infusing fluids into said hub and a third port positioned within the hub for collecting fluid from within the hub; and a guide member for introducing the catheter into the duct, said guide member comprising a distal end including at least one opening for receiving a medicament.

22. The device according to claim 21 wherein the guide member includes a dilator, and wherein said distal end is tapered.

23. The device according to claim 21 wherein the medicament is lidocane.

24. A ductal access device comprising a first elongated member for positioning within a breast duct, said first elongated member comprising an internal lumen, and a manifold hub removably secured to said first elongated member such that said manifold hub can be repeatedly secured to said elongated member and repeatedly separated from said elongated member, said manifold hub including at least three openings in fluid communication with each other and in fluid communication with a proximal end of the first elongated member.

25. The device according to claim 24 wherein said manifold hub includes a first opening that is axially aligned with the internal lumen of the elongated member.

26. The device according to claim 25 wherein said first opening is located at a distal end of the hub that is secured to said elongated member.

27. The device according to claim 26 wherein said manifold hub includes a sidewall carrying an infusion port and a collection port, said infusion port being positioned between the collection port and the first opening.

28. The device according to claim 25 wherein said first opening is positioned at a proximal end of the manifold hub, and a sidewall of the manifold hub extends between the first opening and a distal end of the manifold hub.

29. The device according to claim 28 wherein the distal end of the manifold hub includes an opening in fluid communication with the internal lumen of the elongated member, said sidewall includes a fluid infusion port for delivering fluid to the manifold hub, and the first opening forms a collection port for collecting fluid from said manifold hub.

30. The device according to claim 28 wherein the distal end of the manifold hub includes an opening in fluid communication with the internal lumen of the elongated member, said sidewall includes a fluid collection port for receiving fluid from within the manifold hub, and the first opening forms a fluid infusion port for delivering fluid to the manifold hub.

31. The device according to claim 24 wherein the elongated member comprises a catheter having a distal end that can move between an open position and a closed position.

32. The device according to claim 31 wherein the distal end of the catheter has a first inner diameter when the distal end is in a closed position and a second, larger inner diameter when the distal end is in the open position.

33. The device according to claim 32 further comprising a mechanism for moving the distal end between the open and closed positions.

34. A ductal access device for accessing a breast duct and collecting cellular material from within the duct, said device comprising:

an elongated member comprising a proximal end, a distal end and a lumen extending between the proximal and distal ends;

a hub for being removably secured to said elongated member such that said hub can be separated from said elongated member and securely received within a portion of said elongated member, said hub comprising an infusion port for delivering fluid to the lumen of said elongated member, said infusion port being in fluid communication with an infusion device, and a collection port for receiving fluid and cellular material from within the hub.

35. The device according to claim 34 wherein the lumen of said elongated member is open to the hub.

36. The device according to claim 35 wherein said collection port is in fluid communication with a fluid collection device.

37. The device according to claim 36 wherein the fluid collection device includes a source for creating negative pressure within the hub and a fluid collection line extending between said collection port and the fluid collection device.

38. The device according to claim 35 further including a tubular member extending between said infusion port and the infusion device for delivering fluid from said infusion device to the hub.

39. The device according to claim 35 wherein the hub includes a distal end that is removably positioned within the proximal end of the elongated member.

40. A ductal access device for accessing a breast duct and collecting cellular material from within the duct, said device comprising a first elongated member having a first outer diameter sized for positioning within the breast duct and a second elongated member comprising a second outer diameter that is greater than said first outer diameter for preventing said second elongated member from entering the breast duct, said second elongated member further comprising a sidewall including a plurality of ports in fluid communication with each other and an internal lumen of said first elongated member.

41. The device according to claim 40 wherein the first elongated member comprises a catheter including said internal lumen for introducing fluids into the breast duct and receiving fluid from within the breast duct.

42. The device according to claim 41 wherein said second elongated member comprises a hub including said plurality of ports, said plurality of ports including a first sidewall port, a second sidewall port and a lower port proximate said internal lumen of said first elongated member.

43. The device according to claim 42 wherein the first and second sidewall ports are at the same height along a sidewall of the hub relative to the lower port.

44. The device according to claim 42 wherein the first and second sidewall ports are at different heights along a sidewall of the hub relative to the lower port.

45. The device according to claim 42 further comprising an infusion tube connected to the first sidewall port of the hub; and a collection tube connected to the second sidewall port of the hub.

46. The device according to claim 44 wherein the hub has a volume in the range from about 0.01 cc to 1.0 cc.

47. The device according to claim 41 wherein the diameter of the internal lumen is at least about 0.007 inch.

48. The device according to claim 40 wherein the first elongated member has an outer diameter of no greater than about 0.50 inch.

49. The device according to claim 48 wherein the outer diameter is in the range from about 0.010 inch to 0.050 inch.

50. A ductal access device for accessing a breast duct and collecting cellular material from within the duct, said device comprising a first elongated member having a proximal end, a distal end and an internal lumen extending between said proximal and distal ends; a manifold hub having a proximal end and a distal end, said manifold hub having a lower opening for being in fluid communication with said internal lumen; and an elongated guide member for extending through at least one of the first elongated member and the hub for positioning a portion of the first elongated member in the breast duct, said elongated guide member comprising a distal end including a plurality of openings.

51. The device according to claim 50 wherein the first elongated member comprises a catheter, and a proximal end of said catheter includes a well.

52. The device according to claim 51 wherein said hub includes a distal end that is removably secured within said well after the catheter is positioned in the breast duct and the guide member has been removed from the internal lumen.

53. The device according to claim 52 wherein the distal end of the hub forms a luer lock fit with the well of the catheter.

54. The device according to claim 50 wherein said openings carry a medicament for administering to the lining of the breast duct.

55. A ductal access device for accessing a breast duct and collecting cellular material from within the duct, said device comprising:

a first elongated member having a distal end that can move between an open position and a closed position, a proximal end and an internal lumen extending between said ends; and a manifold hub having a proximal end and a distal end, said manifold hub comprising at least three openings including at least two sidewall openings for receiving fluids and a lower opening for being in fluid communication with said internal lumen.

56. The device according to claim 55 wherein the distal end of the elongated member has a first inner diameter when in the closed position and a second, larger diameter when in the open position.

57. The device according to claim 56 wherein said distal end of the elongated member is formed of a shape memory material that opens in response to the application of a stimulus.

58. The device according to claim 57 wherein said stimulus includes heat or electric current.

59. The device according to claim 57 wherein said shape memory material is Nitinol.

60. The device according to claim 55 wherein said elongated member comprises a catheter, and further including a mechanism for moving the distal opening of said elongated member between the open and closed positions.

61. The device according to claim 60 wherein said mechanism includes a wire extending between the proximal and distal ends of the catheter.

62. A method for lavaging a ductal network in a human breast, said method comprising the steps of:

inserting a distal end of a catheter having an internal lumen through a ductal orifice and into a distal lumen of the ductal network;

infusing a lavage fluid into a manifold hub through an infusion port, said manifold hub being in fluid communication with said internal lumen of said catheter;

introducing the lavage fluid into the ductal network through said internal lumen of said catheter;

withdrawing the lavage fluid and substances borne by the lavage fluid from the ductal network through said internal lumen of said catheter and into said manifold hub; and delivering the withdrawn fluid and substances to a collection device through a collection port in the hub.

63. The method according to claim 62 where said step of infusing lavage fluid into the hub includes delivering the lavage fluid from an infusion device to the infusion port via an infusion tube.

64. The method according to claim 62 wherein the step of withdrawing the lavage fluid and substances includes the step of applying a negative pressure within the hub.

65. The method according to claim 64 wherein the negative pressure is applied by the collection device.

66. The method according to claim 64 wherein the method further includes the step of externally massaging the breast so that the fluid and substances are forced in the direction of the hub.

67. The method according to claim 62 wherein the step of delivering the fluid and substances to the collection device includes infusing fluid into the hub.

68. The method according to claim 62 wherein the step of introducing the lavage fluid into the ductal network includes the step of applying a positive fluid infusion pressure within the hub.

69. A method for obtaining cellular material from a mammalian breast duct network, said method comprising the steps of:

inserting a distal end of an elongated device having an internal lumen through a ductal orifice and into a distal lumen of the ductal network;

infusing a lavage fluid into a manifold hub through an infusion port, said manifold hub being in fluid communication with said internal lumen;

introducing the lavage fluid into the ductal network through said internal lumen of said elongated device;

massaging an area of the breast; and delivering the lavage fluid and substances borne by the lavage fluid from the ductal network to said manifold hub and a collection device through said internal lumen of said elongated device.

70. The method according to claim 69 further including the step of retaining at least 2 mils of the lavage fluid within the breast duct for a predetermined period of time.

71. The method according to claim 70 wherein the predetermined period of time is less than one second.

72. The method according to claim 70 wherein the predetermined period of time is between about one second and one hour.

73. The method according to claim 69 further including the step of creating a negative pressure in at least a portion of the hub.

74. The method according to claim 73 wherein the negative pressure is created by the collection device.

75. The method according to claim 69 wherein a collection tube extends between a collection port on the manifold hub and the collection device.

76. The method according to claim 69 wherein the step of delivering the fluid and substances to the collection device includes infusing fluid into the hub.

77. The method according to claim 69 wherein the step of introducing the lavage fluid into the ductal network includes the step of applying a positive fluid infusion pressure within the hub.

* * * * *